United States Patent
Proehl et al.

(10) Patent No.: US 12,208,123 B2
(45) Date of Patent: Jan. 28, 2025

(54) COMPOSITIONS AND METHODS FOR THE TREATMENT OF SKIN CONDITIONS

(71) Applicant: DERMATA THERAPEUTICS, INC., San Diego, CA (US)

(72) Inventors: Gerald Thomas Proehl, San Diego, CA (US); Christopher Joseph Nardo, San Diego, CA (US)

(73) Assignee: DERMATA THERAPEUTICS, INC., San Diego, CA (US)

( * ) Notice: Subject to any disclaimer, the term of this patent is extended or adjusted under 35 U.S.C. 154(b) by 719 days.

(21) Appl. No.: 17/420,635

(22) PCT Filed: Dec. 26, 2019

(86) PCT No.: PCT/US2019/068598
§ 371 (c)(1),
(2) Date: Jul. 2, 2021

(87) PCT Pub. No.: WO2020/142350
PCT Pub. Date: Jul. 9, 2020

(65) Prior Publication Data
US 2022/0118029 A1 Apr. 21, 2022

Related U.S. Application Data

(60) Provisional application No. 62/788,632, filed on Jan. 4, 2019.

(51) Int. Cl.
| | |
|---|---|
| *A61K 35/614* | (2015.01) |
| *A61K 9/00* | (2006.01) |
| *A61K 35/655* | (2015.01) |
| *A61K 47/02* | (2006.01) |
| *A61P 17/10* | (2006.01) |

(52) U.S. Cl.
CPC .......... *A61K 35/655* (2015.01); *A61K 9/0014* (2013.01); *A61K 47/02* (2013.01); *A61P 17/10* (2018.01)

(58) Field of Classification Search
CPC .................................................. A61K 35/614
See application file for complete search history.

(56) References Cited

U.S. PATENT DOCUMENTS

| | | |
|---|---|---|
| 7,604,821 B2 | 10/2009 | Villani |
| 9,629,856 B2 | 4/2017 | Dreher |
| 2013/0309315 A1 | 11/2013 | Villani |

FOREIGN PATENT DOCUMENTS

| | | |
|---|---|---|
| RU | 2176511 C1 | 12/2001 |
| RU | 2182820 C1 | 5/2002 |
| RU | 2183967 C1 | 6/2002 |
| WO | 02080932 A1 | 10/2002 |
| WO | 2020142350 A1 | 7/2020 |

OTHER PUBLICATIONS

NPS Medicinewise, Radar, Articles, Investigator's Global Assessment (IGA) of acne severity, https://www.nps.org.au/radar/articles/investigators-global-assessment-iga-of-acne-severity-additional-content-adapalene-with-benzoyl-peroxide-epiduo-for-severe-acne-vulgaris, 2011.*
International Search Report and Written Opinion issued in International Application No. PCT/US2019/068598, mailed on Apr. 2, 2020, 14 pages.

* cited by examiner

*Primary Examiner* — Rosanne Kosson
(74) *Attorney, Agent, or Firm* — Mintz, Levin, Cohn, Ferris, Glovsky and Popeo, P.C.

(57) ABSTRACT

The present disclosure relates to the treatment of skin condition in a subject, including acne vulgaris, comprising applying to the skin of the subject a first composition comprising *Spongilla*, and a second composition comprising one or more fluidizing agents, such as water, saline or a hydrogen peroxide solution. The disclosure also relates to a products or kits for the treatment of skin conditions in a subject, including acne vulgaris, comprising *Spongilla*, and a second composition comprising one or more fluidizing agents, such as water, saline or a hydrogen peroxide solution, such as a 3% by weight solution of hydrogen peroxide.

44 Claims, No Drawings

COMPOSITIONS AND METHODS FOR THE TREATMENT OF SKIN CONDITIONS

CROSS REFERENCE

This application claims the priority benefit of U.S. Provisional Application No. 62/788,632, filed Jan. 4, 2019, the details of which are incorporated by reference herein in its entirety.

FIELD

The present disclosure relates to the treatment of skin conditions in a subject, including acne vulgaris, comprising applying to the skin of the subject a first composition comprising *Spongilla*, and a second composition comprising one or more fluidizing agents, such as water, saline or a hydrogen peroxide solution. The disclosure also relates to a products or kits for the treatment of skin conditions in a subject, including acne vulgaris, comprising *Spongilla*, and a second composition comprising one or more fluidizing agents, such as water, saline or a hydrogen peroxide solution, such as a 3% by weight solution of hydrogen peroxide.

BACKGROUND

Acne vulgaris is a common skin disorder that affects approximately 40 million to 50 million Americans and is characterized by comedones, papules, pustules, nodules, and cysts, which most often affect the face, upper chest, upper back, and shoulders. It can be associated with scarring, pigmentary changes, anxiety, social isolation, and decreased mood, self-esteem, and body image. Most individuals develop acne vulgaris at some point during their lives, particularly during adolescence. The exact prevalence varies by population and age. The pathogenesis of acne involves genetic factors, androgen hormones, retention hyperkeratosis, follicular obstruction, elevated sebum production, and proliferation of *Propionibacterium acnes* (*P. acnes*), with associated inflammation. In general, anti-acne medications aim to decrease comedones, *P. acnes*, and inflammation. However, poor patient adherence with anti-acne medications is a common clinical challenge. The prolonged treatment duration required with most anti-acne medications may contribute to this poor patient adherence, as may other factors including the complexity of regimens (e.g., multiple oral and/or topical agents given multiple times per day with restrictions on activities), poor medication tolerability, cosmetically unpleasant formulations, poor patient understanding of the nature of acne, and inappropriate patient expectations in terms of treatment response. Because proper usage of topical therapies is often more complex than is the case for oral therapies, adherence may be a particularly significant issue for topical therapies. Poor patient adherence may contribute to treatment failure, development of resistance to medications, and increased costs. Thus, a topical product with a simple usage paradigm may have the opportunity to exhibit greater treatment success due to improved patient adherence.

A number of skin conditions in subjects have been treated with the topical application of materials derived from naturally occurring sponges, such as *Spongilla lacustris*. The *Spongilla* contains organic and inorganic compounds. The organic compounds have in vitro, anti-inflammatory activity that reduces *P. acnes* stimulated by IL-8 production of NHEK, and antimicrobial effects against *P. acnes*. They may also have an effect on sebum and keratinocyte proliferation by down-regulating the IVL gene in NHEK. The total lipid content is approximately 5% of the biomass of the dried sponge and the protein is composed of spongin or sclerotized collagen. The polysaccharides and N-acetyl-D-glucosamine (NAG) are part of chitin and chitosan that has been reported to be an important component within the skeletal fibers of *Spongilla lacustris* and detected 750±1.5 µg N-acetyl-D-glucosamine per 1 mg of spicule-free skeleton. Chitin and chitosan are described as a family of linear polysaccharides consisting of varying amounts of α or β (1-4) linked residues of N-acetyl-2 amino-2-deoxy-D-glucose and 2-amino-2-deoxy-D glucose residues. In α-chitin, the chains are arranged in sheets or stacks, the chains in any one sheet having the same direction or 'sense'. In β-chitin, adjacent sheets along the c axis have the same direction; the sheets are parallel, while in α-chitin adjacent sheets along the c axis have the opposite direction, they are antiparallel. Chitin is deacetylated into chitosan and can be further degraded into N-acetyl-D-glucosamine (NAG) units. Chitosan preparations are classified into native chitosan, chitosan formulations, complexes and derivatives with other substances. Chitosan can be used to prevent or treat wound and burn infections not only because of its intrinsic antimicrobial properties, but also by virtue of its ability to deliver extrinsic antimicrobial agents to wounds and burns. Chitosan is water-insoluble and highly viscous in dilute acidic solutions. Soluble chitosan oligosaccharides were found to be instrumental in suppressing the LPS-induced nuclear factor kappa-light-chain-enhancer of activated B cell (NF-κB)-dependent inflammatory gene expression, and this was associated with reduced nuclear translocation of NF-κB. Chitosan has also been demonstrated to have an antimicrobial effect against *P. acnes* and *S. aureus*. Chitosan of differing molecular weight (MW) were tested on antibacterial activity, chitosan of low MW (50-190 kDa), medium MW (190-310 kDa), and high MW (310-375+kDa). Concentrations of 2.5, 5, 10, and 20 µg/mL were tested against *P. acnes* with high molecular weight having a greater effect against the gram-positive bacteria *P. acnes* demonstrated in a clinical study that with acne vulgaris subjects, NAG quickly reduced the number of acne lesions over an 8-week period and was better tolerated by the subjects than 10% benzoyl peroxide.

The inventors of the subject matter disclosed herein have discovered that an important component of materials derived from *Spongilla* are the siliceous spicules that comprise the skeletal structure of *Spongilla*. The inventors have discovered the spicules penetrate the stratum corneum of the skin of a subject during application and promote sloughing of the keratinocytes. The inventors of the subject matter disclosed herein have also discovered that the spicules derived from *Spongilla* are useful in facilitating and permitting certain therapeutic compounds and compositions to penetrate into the skin of subjects to which the spicules are applied, which compounds and compositions would otherwise not be able to penetrate the skin of the subject in order to reach their therapeutic targets and treat certain skin conditions. Among the compounds and compositions that may better penetrate the skin in the presence of materials derived from *Spongilla* are products containing a fluidizing agent, such as water, saline or hydrogen peroxide.

The inventors of the subject matter disclosed herein have discovered that a combination of *Spongilla* and one or more fluidizing agents, such as water, saline or a hydrogen peroxide solution, are useful in the treatment of patients, such as those who are 12 years and older, or 9 years and older, with moderate to severe acne vulgaris, including, but not limited to, facial acne vulgaris, moderate facial acne vulgaris, and moderate facial acne vulgaris.

SUMMARY

In one aspect is provided a method of treating a skin condition in a subject, comprising applying to the skin of the subject a first composition comprising *Spongilla*, and a second composition comprising one or more fluidizing agents, such as water, saline or a hydrogen peroxide solution. In one aspect is provided a method of treating a skin condition in a subject comprising applying to the skin of the subject a first composition comprising *Spongilla*, and a second composition comprising a hydrogen peroxide solution. In one aspect is provided any of the methods disclosed herein wherein the hydrogen peroxide solution is 3% by weight aqueous hydrogen peroxide. In one aspect is provided any of the methods disclosed herein wherein the hydrogen peroxide solution is 3% by weight aqueous hydrogen peroxide, and each application of the composition comprises about 2 grams of *Spongilla* and about 6 mL of 3% hydrogen peroxide.

In another aspect is provided a kit, comprising a first composition and a second composition, wherein (a) the first composition comprises a *Spongilla*; and (b) the second composition comprises one or more fluidizing agents. In another aspect is provided a kit comprising a first composition and a second composition, wherein (a) the first composition comprises a *Spongilla*; and (b) the second composition comprises water, saline, or a hydrogen peroxide solution, wherein the kit is used for the treatment of a skin condition in a subject, including acne vulgaris.

In another aspect is provided a composition comprising a first composition and a second composition for use as a medicament, wherein the (a) the first composition comprises a *Spongilla*; and (b) the second composition comprises one or more fluidizing agents. In another aspect is provided such compositions for use as a medicament for the treatment of a skin condition in a subject, such as acne vulgaris, as described herein.

In another aspect is provided a composition comprising a first composition and a second composition for use in the treatment of a skin condition in a subject, including acne vulgaris, including moderate to severe acne vulgaris, wherein (a) the first composition comprising a *Spongilla*; and (b) the second composition comprises one or more fluidizing agents. In another aspect is provided such compositions for use in the treatment of a skin condition in a subject, such as acne vulgaris, as described herein.

In another aspect is provided a composition for the manufacture of a medicament for the treatment of a skin condition in a subject, wherein the composition comprises a first composition and a second composition wherein (a) the first composition comprising a *Spongilla*; and (b) the second composition comprises one or more fluidizing agents.

DETAILED DESCRIPTION

The singular form "a", "an", and "the" include plural references unless the context clearly dictates otherwise. For example, the term "a lesion" includes one or more lesions. "A and/or B" is used herein to include all of the following alternatives: "A", "B", "A or B", and "A and B".

As used herein, the term "about" means either within plus or minus 10% of the provided value, or rounded to the nearest significant figure, in all cases inclusive of the provided value. Where ranges are provided, they are inclusive of the boundary values.

As used herein, the terms "applied," "applying," "administration," "administering," and "used" means the delivery of a composition disclosed herein to a subject, in particular to the skin of the subject, by an administration route including, but not limited to, intraperitoneal, subcutaneous, intramuscular, topically, or any combinations thereof. In some embodiments disclosed herein, the compositions disclosed herein are administered to the subject, in particular to the skin of the subject, by topical administration.

As used herein, the term "aspect ratio" means with respect to the particles of *Spongilla* described herein the ratio between the average length of the particles to the average diameter of the particles.

As used herein, the terms "combination" and "in combination with" mean the application, use, or administration of one or more of the compositions disclosed herein, sequentially or simultaneously. It includes dosing simultaneously, or within minutes or hours of each other, or on the same day, or on alternating days, or using the compositions disclosed herein on a daily basis, or multiple days per week, or weekly basis, for example, while administering another composition on the same day or alternating days or weeks or on a periodic basis during a time simultaneous therewith or concurrent therewith, or at least a part of the time during which the composition disclosed herein is applied, used or administered. For example, one or more of the compositions disclosed herein, could be applied, used, or administered to a subject every day or several days a week while the additional composition is applied, used or dosed on alternating days or alternating weeks or other periods of time, such as every 1, 2, 3, 4, 5, 6, 7, 8, 9, 10, 11, 12, 13, 14 or more days.

As used herein, the term "Dermatology Life Quality Index (DLQI)" means the dermatology-specific, standardized, 10-question, validated questionnaire used by those of ordinary skill in the art to measure the outcome of treatment of subjects suffering from dermatology-related conditions, such as acne vulgaris.

As used herein, the term "inflammatory lesions" includes, but is not limited to (a) papule—a small, red, solid elevation less than 1.0 cm in diameter; (b) pustule—a small, circumscribed elevation of the skin that contains yellow-white exudate; (c) nodule—a circumscribed, elevated, solid lesion generally more than 1.0 cm in diameter with palpable depth; and (d) cyst—a smooth, dome-shaped, elevated, freely moveable, skin-colored, round-to-ovoid lesion greater than 0.7 cm in diameter.

As used herein, the term "noninflammatory lesions" includes, but is not limited to (a) open comedones—a pigmented dilated pilosebaceous orifice (blackhead); and (b) closed comedones—a tiny white papule (whitehead).

The term "Investigator's Global Assessment (IGA) acne severity scale," as used herein, means the scale set forth below that one of ordinary skill in the art may use to measure the severity of acne vulgaris in a patient that is need of treatment.

| Score | Grade | Description |
| --- | --- | --- |
| 0 | None | No evidence of facial acne vulgaris |
| 1 | Minimal | Few non-inflammatory lesions (comedones) are present; a few inflammatory lesions (papules/pustules) may be present; no nodulo-cystic lesions are allowed |

-continued

| Score | Grade | Description |
|---|---|---|
| 2 | Mild | Several to many non-inflammatory lesions (comedones) are present; a few inflammatory lesions (papules/pustules) are present; no nodulo-cystic lesions are allowed |
| 3 | Moderate | Many non-inflammatory lesions (comedones) and inflammatory lesions (papules/pustules) are present; no nodulo-cystic lesions are allowed |
| 4 | Severe | Significant degree of inflammatory disease; papules/pustules are a predominate feature; a few nodulo-cystic lesions may be present; comedones may be present |

The term "*Spongilla*" as used herein means a genus of freshwater sponges in the family Spongillidae, including, but not limited to, *Spongilla lacustris, S. fragilis* Leidy, and *Ephydatia fluviatilis*. The term "*Spongilla lacustris*" as used herein means a species of sponge of the freshwater sponge family Spongillidae.

The terms "composition comprising *Spongilla*," "powders comprising *Spongilla*," "materials comprising *Spongilla*, "*Spongilla* in the form of a powder," and the like, as used herein, mean materials comprising *Spongilla* derived from raw *Spongilla* that is harvested and processed and may include all the various components of the *Spongilla* following harvest, including all organic and/or inorganic compounds and materials that are part of the naturally-occurring *Spongilla*, or may include only a portion of the organic and/or inorganic compounds and materials that are part of the naturally-occurring *Spongilla*. In one aspect is provided any of the methods or kits disclosed herein, wherein the *Spongilla* materials comprise all or substantially all the organic and inorganic materials derived from the naturally occurring *Spongilla*. In another aspect is provided any of the methods or kits disclosed herein, wherein the *Spongilla* materials comprise (a) only the spicules and any materials that are naturally associated with the spicules, or (b) substantially purified spicules and any materials that are naturally associated with the spicules, or (c) purified spicules and any materials that are naturally associated with the spicules that are a component part of naturally-occurring *Spongilla*. In another aspect is provided any of the methods or kits disclosed herein, wherein the *Spongilla* materials comprise only the spicules and any materials that are naturally associated with the spicules. In another aspect is provided any of the methods or kits disclosed herein, wherein the *Spongilla* materials comprise substantially purified spicules and any materials that are naturally associated with the spicules. In another aspect is provided any of the methods or kits disclosed herein, wherein the *Spongilla* materials comprise purified spicules and any materials that are naturally associated with the spicules that are a component part of naturally occurring *Spongilla*.

As used herein, the term "subject" means a mammal, including a human, a dog, a cat, cattle, or a pig. In one embodiment the subject is a human. In one embodiment, the subject is a dog. In one embodiment, the subject is a cat. In one embodiment, the subject is cattle. In one embodiment, the subject is a pig.

As used herein, the term "therapeutically effective amount" means that amount of the composition or combination of compositions being applied, used or administered to a subject that will treat, relieve, or prevent to some extent one or more of the symptoms of the disorder being treated, including the reduction of the number of acne lesions on the skin of subject, and/or an improvement in subjects IGA score, each following treatment with the composition compared to the baseline number of acne lesions and/or IGA score prior to treatment with the composition.

*Spongilla*, including *Spongilla lacustris*, and powders prepared from *Spongilla* that are utilized in the methods disclosed herein may be obtained, processed and characterized by methods known to those having ordinary skill in the art. For example, U.S. Pat. No. 7,604,821 describes the harvest, processing and characterization of several species of *Spongilla*, including *Spongilla lacustris*. The disclosure of U.S. Pat. No. 7,604,821 is incorporated herein by reference in its entirety. Sponge materials may be collected using methods commonly known to those skilled in the art of marine biology. For example, sponges can be collected manually using basic under water diving techniques, or in deeper waters larger colonies are harvested using the Agassiz trawl (AGT) or epibenthic sledge (EBS). Under certain environmental conditions, *Spongilla* colonies occur in a thin crust-like carpet several meters across and must be collected manually, with fork-like tools, and nets. The collected sponge mass is dried, cleaned of gross contamination, such as shells, stems, plants, rocks and other impurities, and is then washed to remove dirt, sand, silt and soluble impurities. The cleaned sponge mass is weighed and dried using methods known to those of ordinary skill in the art, such as air drying and the use of dryers that are used to dehydrate foods and pharmaceuticals. The sponge mass is dried until residual moisture content is less than a desired value as further disclosed herein. Residual moisture measurements can be performed using methods commonly known in the arts of food sciences, analytical chemistry or the pharmaceutical sciences. For example, 10 grams of dried material may be placed on a tared weighing boat and then weighed. The weighed material is then exposed to a heat source such as a drying oven or heat lamp operated at an appropriate temperature, the sample is then cooled in a desiccated chamber and re-weighed. Residual moisture is calculated as the percent difference between the sample weight before drying and the weight after cooling. Following drying, the sponge materials may be packaged in sealed containers, which optionally protect the materials from light, moisture and oxygen. The materials may then be further tested for the presence of pathogens, coliform organisms and organisms that represent a bioburden. The materials may be further heated or irradiated, as disclosed herein, to reduce any pathogens, coliform organisms or other organisms that represent a bioburden. The materials may then be further processed using methods known to those having ordinary skill in the art to provide a powder comprising particles having a desired size. For example, the sponge materials may be ground, and the resulting materials passed through one or more sieves of a defined size to provide a resulting material comprising particles having a uniform, or substantially uniform size. After final processing and sizing processes are completed, the dried sponge material may be packaged in airtight moisture-proof containers and stored at an appropriate temperature, such as at about room or ambient temperature.

In one aspect is provided a method of treating a skin condition in a subject, comprising applying to the skin of the subject a first composition comprising *Spongilla*, and a second composition comprising one or more fluidizing agents as described herein, including 3% w/w hydrogen peroxide. In some embodiments, the subject experiences a reduction in the number of acne vulgaris inflammatory lesions and/or non-inflammatory lesions following application of a mixture of the first composition and the second composition. In some embodiments, the subject experiences a reduction in the number of inflammatory lesions following application of a mixture of the first composition and the second composition. In some embodiments, the subject experiences a reduction in the number of non-inflammatory lesions following application of a mixture of the first composition and the second composition. In some embodiments, the subject experiences a 2-grade change in the Investigator's Global Assessment (IGA) acne severity scale following application of a mixture of the first composition and the second composition. In some embodiments, the subject experiences a 2-grade change in the Investigator's Global Assessment (IGA) acne severity scale and an IGA score of 0 or 1 following application of a mixture of the first composition and the second composition. In some embodiments, the grade changes in the Investigator's Global Assessment (IGA) acne severity scale are measured at one, two, three, four, five, six, seven, eight, nine, 10, 11, 12, 13, 14, 15, 16, 17, 18, 19, 20, 21, 22, 23, 24, 28, 32, 36, 40, 44, 48, or 52 weeks following treatment. In some embodiments, the grade changes in the Investigator's Global Assessment (IGA) acne severity scale are measured at 12 weeks following treatment.

In another aspect is provided a composition comprising a first composition and a second composition for use as a medicament, wherein the (a) the first composition comprises a *Spongilla*; and (b) the second composition one or more fluidizing agents. In another aspect is provided a composition comprising a first composition and a second composition for use as a medicament, wherein the (a) the first composition comprises a *Spongilla lacustris*; and (b) the second composition one or more fluidizing agents. The medicament may be used to treat a skin condition in a subject, including acne vulgaris. The fluidizing agent(s) may be as described herein, including 3% w/w hydrogen peroxide. In some embodiments, the subject experiences a reduction in the number of acne vulgaris inflammatory lesions and/or non-inflammatory lesions following application of the composition. In some embodiments, the subject experiences a reduction in the number of inflammatory lesions following application of the composition. In some embodiments, the subject experiences a reduction in the number of non-inflammatory lesions following application of the composition. In some embodiments, the subject experiences a 2-grade change in the Investigator's Global Assessment (IGA) acne severity scale following application of the composition. In some embodiments, the subject experiences a 2-grade change in the Investigator's Global Assessment (IGA) acne severity scale and an IGA score of 0 or 1 following application of the composition.

In another aspect is provided a composition comprising a first composition and a second composition for use in the treatment of a skin condition in a subject, wherein (a) the first composition comprising a *Spongilla*; and (b) the second composition one or more fluidizing agents. In another aspect is provided a combination comprising a first composition and a second composition for use in the treatment of a skin condition in a subject, wherein (a) the first composition comprising a *Spongilla lacustris*; and (b) the second composition one or more fluidizing agents. The composition may be used to treat a skin condition in a subject, including acne vulgaris. The fluidizing agent(s) may be as described herein, including 3% w/w hydrogen peroxide. In some embodiments, the subject experiences a reduction in the number of acne vulgaris inflammatory lesions and/or non-inflammatory lesions following application of the composition. In some embodiments, the subject experiences a reduction in the number of inflammatory lesions following application of the composition. In some embodiments, the subject experiences a reduction in the number of non-inflammatory lesions following application of the composition. In some embodiments, the subject experiences a 2-grade change in the Investigator's Global Assessment (IGA) acne severity scale following application of the composition. In some embodiments, the subject experiences a 2-grade change in the Investigator's Global Assessment (IGA) acne severity scale and an IGA score of 0 or 1 following application of the composition.

In another aspect is provided a composition for the manufacture of a medicament for the treatment of a skin condition in a subject, wherein the composition comprises a first composition and a second composition wherein (a) the first composition comprising a *Spongilla*; and (b) the second composition one or more fluidizing agents. In another aspect is provided a composition for the manufacture of a medicament for the treatment of a skin condition in a subject, wherein the composition comprises a first composition and a second composition wherein (a) the first composition comprising a *Spongilla lacustris*; and (b) the second composition one or more fluidizing agents. The medicament may be used to treat a skin condition in a subject, including acne vulgaris. The fluidizing agent(s) may be as described herein, including 3% w/w hydrogen peroxide. In some embodiments, the subject experiences a reduction in the number of acne vulgaris inflammatory lesions and/or non-inflammatory lesions following use of the medicament. In some embodiments, the subject experiences a reduction in the number of inflammatory lesions following use of the medicament. In some embodiments, the subject experiences a reduction in the number of non-inflammatory lesions following use of the medicament. In some embodiments, the subject experiences a 2-grade change in the Investigator's Global Assessment (IGA) acne severity scale following use of the medicament. In some embodiments, the subject experiences a 2-grade change in the Investigator's Global Assessment (IGA) acne severity scale and an IGA score of 0 or 1 following use of the medicament.

In another aspect is provided a method for treating acne vulgaris in a subject, comprising administering to the subject a pharmaceutical composition comprising a first composition and a second composition, wherein the first composition comprises *Spongilla*, and the second composition comprises one or more fluidizing agents, wherein the pharmaceutical composition is applied to an area of the skin of the subject in need of treatment. The fluidizing agent(s) may be as described herein, including 3% w/w hydrogen peroxide. In some embodiments, the subject experiences a reduction in the number of acne vulgaris inflammatory lesions and/or non-inflammatory lesions following application of the pharmaceutical composition. In some embodiments, the subject experiences a reduction in the number of inflammatory lesions following application of the pharmaceutical composition. In some embodiments, the subject experiences a reduction in the number of non-inflammatory lesions following application of the pharmaceutical composition. In some embodiments, the subject experiences a 2-grade change in the Investigator's Global Assessment (IGA) acne severity scale following application of the pharmaceutical composition. In some embodiments, the subject experiences a 2-grade change in the Investigator's Global Assessment (IGA) acne severity scale and an IGA score of 0 or 1 following application of the pharmaceutical composition.

In another aspect is provided a method of treating acne vulgaris in a subject, comprising applying to the skin of the subject in need of treatment a pharmaceutical composition comprising a first composition and a second composition, wherein the first composition comprises *Spongilla*, and the second composition comprises one or more fluidizing agents, wherein the pharmaceutical composition is applied to the skin of the subject in need of treatment. The fluidizing agent(s) may be as described herein, including 3% w/w hydrogen peroxide. In some embodiments, the subject experiences a reduction in the number of acne vulgaris inflammatory lesions and/or non-inflammatory lesions following application of the pharmaceutical composition. In some embodiments, the subject experiences a reduction in the number of inflammatory lesions following application of the pharmaceutical composition. In some embodiments, the subject experiences a reduction in the number of non-inflammatory lesions following application of the pharmaceutical composition. In some embodiments, the subject experiences a 2-grade change in the Investigator's Global Assessment (IGA) acne severity scale following application of the pharmaceutical composition. In some embodiments, the subject experiences a 2-grade change in the Investigator's Global Assessment (IGA) acne severity scale and an IGA score of 0 or 1 following application of the pharmaceutical composition.

In another aspect is provided a method of treating or preventing acne vulgaris in a subject, comprising applying to the skin of the subject in need of treatment a mixture comprising *Spongilla* and one or more fluidizing agents. The fluidizing agent(s) may be as described herein, including 3% w/w hydrogen peroxide. In some embodiments, the subject experiences a reduction in the number of acne vulgaris inflammatory lesions and/or non-inflammatory lesions following application of a mixture of the first composition and the second composition. In some embodiments, the subject experiences a reduction in the number of inflammatory lesions following application of a mixture of the first composition and the second composition. In some embodiments, the subject experiences a reduction in the number of non-inflammatory lesions following application of a mixture of the first composition and the second composition. In some embodiments, the subject experiences a 2-grade change in the Investigator's Global Assessment (IGA) acne severity scale following application of a mixture of the first composition and the second composition. In some embodiments, the subject experiences a 2-grade change in the Investigator's Global Assessment (IGA) acne severity scale and an IGA score of 0 or 1 following application of a mixture of the first composition and the second composition.

In another aspect is provided a method of reducing the number of acne vulgaris lesions on the skin of a subject, comprising applying to an area of the skin of the subject in need of treatment a mixture comprising *Spongilla* and one or more fluidizing agents. The fluidizing agent(s) may be as described herein, including 3% w/w hydrogen peroxide. In some embodiments, the subject experiences a reduction in the number of inflammatory lesions and/or non-inflammatory lesions following application of the mixture. In some embodiments, the subject experiences a reduction in the number of inflammatory lesions following application of the mixture. In some embodiments, the subject experiences a reduction in the number of non-inflammatory lesions following application of the mixture. In some embodiments, the subject experiences a reduction in the number of acne vulgaris inflammatory lesions and/or non-inflammatory lesions following application of a mixture of the first composition and the second composition. In some embodiments, the subject experiences a reduction in the number of inflammatory lesions following application of a mixture of the first composition and the second composition. In some embodiments, the subject experiences a reduction in the number of non-inflammatory lesions following application of a mixture of the first composition and the second composition. In some embodiments, the subject experiences a 2-grade change in the Investigator's Global Assessment (IGA) acne severity scale following application of a mixture of the first composition and the second composition. In some embodiments, the subject experiences a 2-grade change in the Investigator's Global Assessment (IGA) acne severity scale and an IGA score of 0 or 1 following application of a mixture of the first composition and the second composition.

In another aspect is provided a method of reducing the number of acne vulgaris lesions on the skin of a subject, comprising applying to an area of the skin of the subject in need of treatment a first composition comprising *Spongilla*, and a second composition comprising one or more fluidizing agents. The fluidizing agent(s) may be as described herein, including 3% w/w hydrogen peroxide. In some embodiments, the subject experiences a reduction in the number of acne vulgaris inflammatory lesions and/or non-inflammatory lesions following application of a mixture of the first composition and the second composition. In some embodiments, the subject experiences a reduction in the number of inflammatory lesions following application of a mixture of the first composition and the second composition. In some embodiments, the subject experiences a reduction in the number of non-inflammatory lesions following application of a mixture of the first composition and the second composition. In some embodiments, the subject experiences a 2-grade change in the Investigator's Global Assessment (IGA) acne severity scale following application of a mixture of the first composition and the second composition. In some embodiments, the subject experiences a 2-grade change in the Investigator's Global Assessment (IGA) acne severity scale and an IGA score of 0 or 1 following application of a mixture of the first composition and the second composition.

In another aspect is provided a method of reducing the number of acne vulgaris lesions on the skin of a subject, comprising administering to the subject a pharmaceutical composition comprising a first composition and a second composition, wherein the first composition comprises *Spongilla*, and the second composition comprises one or more fluidizing agents, wherein the pharmaceutical composition is applied to an area of the skin of the subject in need of treatment. The fluidizing agent(s) may be as described herein, including 3% w/w hydrogen peroxide. In some embodiments, the subject experiences a reduction in the number of acne vulgaris inflammatory lesions and/or non-inflammatory lesions following application of a mixture of the pharmaceutical composition. In some embodiments, the subject experiences a reduction in the number of inflammatory lesions following application of the pharmaceutical composition. In some embodiments, the subject experiences a reduction in the number of non-inflammatory lesions following application the pharmaceutical composition. In some embodiments, the subject experiences a 2-grade change in the Investigator's Global Assessment (IGA) acne severity scale following application of the pharmaceutical composition. In some embodiments, the subject experiences a 2-grade change in the Investigator's Global Assessment (IGA) acne severity scale and an IGA score of 0 or 1 following application of the pharmaceutical composition.

In another aspect is provided any of the methods disclosed herein, wherein treatment comprises one or more applications to the skin of the subject of the first composition comprising *Spongilla*, and the second composition comprising one or more fluidizing agents. The fluidizing agent(s) may be as described herein, including 3% w/w hydrogen peroxide. In some embodiments, the subject experiences a reduction in the number of acne vulgaris inflammatory lesions and/or non-inflammatory lesions following application of a mixture of the first composition and the second composition. In some embodiments, the subject experiences a reduction in the number of inflammatory lesions following application of a mixture of the first composition and the second composition. In some embodiments, the subject experiences a reduction in the number of non-inflammatory lesions following application of a mixture of the first composition and the second composition. In some embodiments, the subject experiences a 2-grade change in the Investigator's Global Assessment (IGA) acne severity scale following application of a mixture of the first composition and the second composition. In some embodiments, the subject experiences a 2-grade change in the Investigator's Global Assessment (IGA) acne severity scale and an IGA score of 0 or 1 following application of a mixture of the first composition and the second composition.

In another aspect is provided any of the methods disclosed herein, wherein the one or more fluidizing agents is applied to the skin of the subject in the form of a pharmaceutical composition comprising the one or more fluidizing agents and one or more pharmaceutically acceptable carriers or excipients. In another aspect is provided any of the methods disclosed herein, wherein the second composition is in the form of a solution, an aqueous solution, a powder, or a gel. The fluidizing agent(s) may be as described herein, including 3% w/w hydrogen peroxide.

In another aspect is provided any of the methods disclosed herein, wherein the subject experiences a reduction in the total number of acne vulgaris lesions following treatment with the composition. In another aspect is provided any of the methods disclosed herein, wherein the subject experiences a reduction in the total number of acne vulgaris lesions of at least 10% following treatment with the composition. In another aspect is provided any of the methods disclosed herein, wherein the total number of acne vulgaris lesions on the skin of the subject is reduced by at least 20% following treatment with the composition. In another aspect is provided any of the methods disclosed herein, wherein the total number of acne vulgaris lesions on the skin of the subject is reduced by at least 30% following treatment with the composition. In another aspect is provided any of the methods disclosed herein, wherein the total number of acne vulgaris lesions on the skin of the subject is reduced by at least 40% following treatment with the composition. In another aspect is provided any of the methods disclosed herein, wherein the total number of acne vulgaris lesions on the skin of the subject is reduced by at least 50% following treatment with the composition. In another aspect is provided any of the methods disclosed herein, wherein the total number of acne vulgaris lesions on the skin of the subject is reduced by at least 60% following treatment. In another aspect is provided any of the methods disclosed herein, wherein the total number of acne vulgaris lesions on the skin of the subject is reduced by at least 70% following treatment. In another aspect is provided any of the methods disclosed herein, wherein the total number of acne vulgaris lesions on the skin of the subject is reduced by at least 80% following treatment. In another aspect is provided any of the methods disclosed herein, wherein the total number of acne vulgaris lesions on the skin of the subject is reduced by at least 90% following treatment. In all cases, the reduction in the number of acne vulgaris lesions following treatment is measured compared to the baseline number of acne vulgaris lesions prior to treatment with the composition in an area of the skin to be treated.

In another aspect is provided any of the methods disclosed herein, wherein the subject experiences a reduction in the total number of inflammatory acne vulgaris lesions following treatment with the composition. In another aspect is provided any of the methods disclosed herein, wherein the subject experiences a reduction in the total number of inflammatory acne vulgaris lesions of at least 10% following treatment with the composition. In another aspect is provided any of the methods disclosed herein, wherein the total number of inflammatory acne vulgaris lesions on the skin of the subject is reduced by at least 20% following treatment with the composition. In another aspect is provided any of the methods disclosed herein, wherein the total number of inflammatory acne vulgaris lesions on the skin of the subject is reduced by at least 30% following treatment with the composition. In another aspect is provided any of the methods disclosed herein, wherein the total number of inflammatory acne vulgaris lesions on the skin of the subject is reduced by at least 40% following treatment with the composition. In another aspect is provided any of the methods disclosed herein, wherein the total number of inflammatory acne vulgaris lesions on the skin of the subject is reduced by at least 50% following treatment with the composition. In another aspect is provided any of the methods disclosed herein, wherein the total number of inflammatory acne vulgaris lesions on the skin of the subject is reduced by at least 60% following treatment. In another aspect is provided any of the methods disclosed herein, wherein the total number of inflammatory acne vulgaris lesions on the skin of the subject is reduced by at least 70% following treatment. In another aspect is provided any of the methods disclosed herein, wherein the total number of inflammatory acne vulgaris lesions on the skin of the subject is reduced by at least 80% following treatment. In another aspect is provided any of the methods disclosed herein, wherein the total number of inflammatory acne vulgaris lesions on the skin of the subject is reduced by at least 90% following treatment. In all cases, the reduction in the number of inflammatory acne vulgaris lesions following treatment is measured compared to the baseline number of acne vulgaris lesions prior to treatment with the composition in an area of the skin to be treated.

In another aspect is provided any of the methods disclosed herein, wherein the subject experiences a reduction in the total number of non-inflammatory acne vulgaris lesions following treatment with the composition. In another aspect is provided any of the methods disclosed herein, wherein the subject experiences a reduction in the total number of non-inflammatory acne vulgaris lesions of at least 10% following treatment with the composition. In another aspect is provided any of the methods disclosed herein, wherein the total number of non-inflammatory acne vulgaris lesions on the skin of the subject is reduced by at least 20% following treatment with the composition. In another aspect is provided any of the methods disclosed herein, wherein the total number of non-inflammatory acne vulgaris lesions on the skin of the subject is reduced by at least 30% following treatment with the composition. In another aspect is provided any of the methods disclosed herein, wherein the total number of non-inflammatory acne vulgaris lesions on the skin of the subject is reduced by at least 40% following treatment with the composition. In another aspect is provided any of the methods disclosed herein, wherein the total number of non-inflammatory acne vulgaris lesions on the skin of the subject is reduced by at least 50% following treatment with the composition. In another aspect is provided any of the methods disclosed herein, wherein the total number of non-inflammatory acne vulgaris lesions on the skin of the subject is reduced by at least 60% following treatment. In another aspect is provided any of the methods disclosed herein, wherein the total number of non-inflammatory acne vulgaris lesions on the skin of the subject is reduced by at least 70% following treatment. In another aspect is provided any of the methods disclosed herein, wherein the total number of non-inflammatory acne vulgaris lesions on the skin of the subject is reduced by at least 80% following treatment. In another aspect is provided any of the methods disclosed herein, wherein the total number of non-inflammatory acne vulgaris lesions on the skin of the subject is reduced by at least 90% following treatment. In all cases, the reduction in the number of non-inflammatory acne vulgaris lesions following treatment is measured compared to the baseline number of acne vulgaris lesions prior to treatment with the composition in an area of the skin to be treated.

In another aspect is provided any of the methods disclosed herein, wherein the total number of acne vulgaris lesions on the skin of the subject is reduced by from about 10% to about 20%, or from about 10% to about 30%, or from about 10% to about 40%, or from about 10% to about 50%, or from about 10% to about 60%, or from about 10% to about 70%, or from about 10% to about 80%, or from about 10% to about 90%, or from about 10% to about 95%, or from about 10% to about 99%, or from about 25% to about 50%, or from about 25% to about 75%, or from about 25% to about 90%, or from about 30% to about 50%, or from about 30% to about 75%, or from about 30% to about 85%, or from about 30% to about 90%, or from about 30% to about 95%, or from about 30% to about 99%, or from about 50% to about 75%, or from about 50% to about 85%, or from about 50% to about 95%, or from about 50% to about 99%, or from about 75% to about 95% or from about 75% to about 99% following treatment with the composition. In all cases, the reduction in the number of acne vulgaris lesions following treatment is measured compared to the baseline number of acne vulgaris lesions prior to treatment with the composition in the area of the skin to be treated.

In another aspect is provided any of the methods disclosed herein, wherein the total number of inflammatory acne vulgaris lesions on the skin of the subject is reduced by from about 10% to about 20%, or from about 10% to about 30%, or from about 10% to about 40%, or from about 10% to about 50%, or from about 10% to about 60%, or from about 10% to about 70%, or from about 10% to about 80%, or from about 10% to about 90%, or from about 10% to about 95%, or from about 10% to about 99%, or from about 25% to about 50%, or from about 25% to about 75%, or from about 25% to about 90%, or from about 30% to about 50%, or from about 30% to about 75%, or from about 30% to about 85%, or from about 30% to about 90%, or from about 30% to about 95%, or from about 30% to about 99%, or from about 50% to about 75%, or from about 50% to about 85%, or from about 50% to about 95%, or from about 50% to about 99%, or from about 75% to about 95% or from about 75% to about 99% following treatment with the composition. In all cases, the reduction in the number of inflammatory acne vulgaris lesions following treatment is measured compared to the baseline number of inflammatory acne vulgaris lesions prior to treatment with the composition in the area of the skin to be treated.

In another aspect is provided any of the methods disclosed herein, wherein the total number of non-inflammatory acne vulgaris lesions on the skin of the subject is reduced by from about 10% to about 20%, or from about 10% to about 30%, or from about 10% to about 40%, or from about 10% to about 50%, or from about 10% to about 60%, or from about 10% to about 70%, or from about 10% to about 80%, or from about 10% to about 90%, or from about 10% to about 95%, or from about 10% to about 99%, or from about 25% to about 50%, or from about 25% to about 75%, or from about 25% to about 90%, or from about 30% to about 50%, or from about 30% to about 75%, or from about 30% to about 85%, or from about 30% to about 90%, or from about 30% to about 95%, or from about 30% to about 99%, or from about 50% to about 75%, or from about 50% to about 85%, or from about 50% to about 95%, or from about 50% to about 99%, or from about 75% to about 95% or from about 75% to about 99% following treatment with the composition. In all cases, the reduction in the number of non-inflammatory acne vulgaris lesions following treatment is measured compared to the baseline number of non-inflammatory acne vulgaris lesions prior to treatment with the composition in the area of the skin to be treated.

In another aspect is provided any of the methods disclosed herein, wherein the subject experiences an improvement from baseline in the Investigator's Global Assessment (IGA) acne severity scale following treatment with the composition. In another aspect is provided any of the methods disclosed herein, wherein the subject experiences at least a one-grade improvement in the Investigator's Global Assessment (IGA) acne severity scale following treatment with the composition. In another aspect is provided any of the methods disclosed herein, wherein the subject experiences at least a two-grade improvement in the Investigator's Global Assessment (IGA) acne severity scale following treatment. In another aspect is provided any of the methods disclosed herein, wherein the subject experiences at least a three-grade improvement in the Investigator's Global Assessment (IGA) acne severity scale following treatment. In another aspect is provided any of the methods disclosed herein, wherein the subject experiences at least a four-grade improvement in the Investigator's Global Assessment (IGA) acne severity scale following treatment with the composition. In another aspect is provided any of the methods disclosed herein, wherein the subject has a score of 2 or less on the Investigator's Global Assessment (IGA) acne severity scale following treatment with the composition. In another aspect is provided any of the methods disclosed herein, wherein the subject has a score of 1 or less on the Investigator's Global Assessment (IGA) acne severity scale following treatment with the composition. In another aspect is provided any of the methods disclosed herein, wherein the subject has a score of zero on the Investigator's Global Assessment (IGA) acne severity scale following treatment with the composition. In another aspect is provided any of the methods disclosed herein, wherein the subject has a score of 3 or 4 on the Investigator's Global Assessment (IGA) acne severity scale prior to treatment and a score of 2, 1, or zero on the Investigator's Global Assessment (IGA) acne severity scale following treatment with the composition. In another aspect is provided any of the methods disclosed herein, wherein the subject has a score of 4 on the Investigator's Global Assessment (IGA) acne severity scale prior to treatment with the composition. In another aspect is provided any of the methods disclosed herein, wherein the subject has a score of 3 on the Investigator's Global Assessment (IGA) acne severity scale prior to treatment with the composition.

In another aspect is provided any of the methods disclosed herein, wherein the subject experiences a 2-grade improvement from baseline in the Investigator's Global Assessment (IGA) acne severity scale following treatment with the composition. In another aspect is provided any of the methods disclosed herein, wherein the subject experiences (a) a 2-grade improvement from baseline in the Investigator's Global Assessment (IGA) acne severity scale, and (b) an IGA score of zero or one following treatment with the composition.

In another aspect is provided any of the methods disclosed herein, wherein the subject experiences a decrease in the subject's total score in Dermatology Life Quality Index (DLQI) following treatment with the composition compared to the subject's score in Dermatology Life Quality Index (DLQI) prior to treatment. In another aspect is provided any of the methods disclosed herein, wherein the subject experiences a decrease of at least one point in the subject's total score in Dermatology Life Quality Index (DLQI) following treatment with the composition compared to the subject's score in Dermatology Life Quality Index (DLQI) prior to treatment. In another aspect is provided any of the methods disclosed herein, wherein the subject experiences a decrease of at least two points in the subject's total score in Dermatology Life Quality Index (DLQI) following treatment with the composition compared to the subject's score in Dermatology Life Quality Index (DLQI) prior to treatment. In another aspect is provided any of the methods disclosed herein, wherein the subject experiences a decrease of at least three points in the subject's total score in Dermatology Life Quality Index (DLQI) following treatment with the composition compared to the subject's score in Dermatology Life Quality Index (DLQI) prior to treatment. In another aspect is provided any of the methods disclosed herein, wherein the subject experiences a decrease of at least four points in the subject's total score in Dermatology Life Quality Index (DLQI) following treatment with the composition compared to the subject's score in Dermatology Life Quality Index (DLQI) prior to treatment.

In another aspect is provided any of the methods disclosed herein, wherein the subject is not diagnosed with acne excoriate, acne conglobate, acne fulminans, secondary acne, chloracne, iatrogenic acne, drug-induced acne, or 1 or 2 or more nodule or cyst above the mandibular line. In another aspect is provided any of the methods disclosed herein, wherein the subject is not pregnant or lactating during the treatment period. In another aspect is provided any of the methods disclosed herein, wherein the patient is not allergic to shellfish or iodine. In another aspect is provided any of the methods disclosed herein, wherein the subject does not have a history of suffering from infection with herpes simplex virus in the area of the skin of the subject to be treated. In another aspect is provided any of the methods disclosed herein, wherein the subject is 12 years of age or older. In another aspect is provided any of the methods disclosed herein, wherein the subject does not suffer from basal cell carcinoma in the area of the skin of the subject to be treated.

In another aspect is provided any of the methods disclosed herein, wherein the subject has (a) from about 20 but not more than 50 inflammatory lesions (papules and pustules) on the face; (b) from about 20 but not more than 100 noninflammatory lesions (open comedones and closed comedones) on the face; or (c) an investigator's Global Assessment (IGA) score of 3 or 4 in the area of the skin to be treated. In another aspect is provided any of the methods disclosed herein, wherein the subject from about 20 but not more than 50 inflammatory lesions (papules and pustules) on the area of the face to be treated. In another aspect is provided any of the methods disclosed herein, wherein the subject has from about 20 but not more than 100 noninflammatory lesions (open comedones and closed comedones) in the area of the face to be treated. In another aspect is provided any of the methods disclosed herein, wherein the subject has an investigator's Global Assessment (IGA) score of 3 or 4 in the area of the skin to be treated. In another aspect is provided any of the methods disclosed herein, wherein the subject has (a) from about 20 to 30 inflammatory lesions (papules and pustules) on the face; (b) from about 20 noninflammatory lesions (open comedones and closed comedones) on the face; or (c) an investigator's Global Assessment (IGA) score of 3 or 4 in the area of the skin to be treated. In another aspect is provided any of the methods disclosed herein, wherein the subject from about 20 to 30 inflammatory lesions (papules and pustules) on the area of the face to be treated. In another aspect is provided any of the methods disclosed herein, wherein the subject has from about 20 noninflammatory lesions (open comedones and closed comedones) in the area of the face to be treated. In another aspect is provided any of the methods disclosed herein, wherein the subject has an investigator's Global Assessment (IGA) score of 3 or 4 in the area of the skin to be treated. In another aspect is provided any of the methods disclosed herein, wherein the subject has no more than 2 nodules or cysts.

In another aspect is provided any of the methods and/or kits disclosed herein, wherein the one or more fluidizing agents is selected from water, saline, and a hydrogen peroxide solution. In another aspect is provided any of the methods and/or kits disclosed herein, wherein the fluidizing agent is water. In another aspect is provided any of the methods and/or kits disclosed herein, wherein the fluidizing agent is saline. In another aspect is provided any of the methods and/or kits disclosed herein, wherein the fluidizing agent is a hydrogen peroxide solution. In another aspect is provided any of the methods and/or kits disclosed herein, wherein the hydrogen peroxide solution is an aqueous solution. In another aspect is provided any of the methods and/or kits disclosed herein, wherein the hydrogen peroxide solution is from about 0.5% by weight to about 50% by weight hydrogen peroxide. In another aspect is provided any of the methods and/or kits disclosed herein, wherein the hydrogen peroxide solution is about 0.5% w/w, about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 15% w/w, about 25% w/w, about 30% w/w, about 35% w/w, about 40% w/w, about 45% w/w, or about 50% w/w. In another aspect is provided any of the methods and/or kits disclosed herein, wherein the hydrogen peroxide solution is about 1% by weight hydrogen peroxide. In another aspect is provided any of the methods and/or kits disclosed herein, wherein the hydrogen peroxide solution is about 2% by weight hydrogen peroxide. In another aspect is provided any of the methods and/or kits disclosed herein, wherein the hydrogen peroxide solution is about 3% by weight hydrogen peroxide. In another aspect is provided any of the methods and/or kits disclosed herein, wherein the hydrogen peroxide solution is about 4% by weight hydrogen peroxide. In another aspect is provided any of the methods and/or kits disclosed herein, wherein the hydrogen peroxide solution is about 5% by weight hydrogen peroxide. In another aspect is provided any of the methods and/or kits disclosed herein, wherein the hydrogen peroxide solution is about 6% by weight hydrogen peroxide. In another aspect is provided any of the methods and/or kits disclosed herein, wherein the hydrogen peroxide solution is about 7% by weight hydrogen peroxide. In another aspect is provided any of the methods and/or kits disclosed herein, wherein the hydrogen peroxide solution is about 8% by weight hydrogen peroxide. In another aspect is provided any of the methods and/or kits disclosed herein, wherein the hydrogen peroxide solution is about 9% by weight hydrogen peroxide. In another aspect is provided any of the methods and/or kits disclosed herein, wherein the hydrogen peroxide solution is about 10% by weight hydrogen peroxide. In another aspect is provided any of the methods and/or kits disclosed herein, wherein the hydrogen peroxide is at a concentration of from about 0.1% w/w to about 50% w/w, or from about 0.1% w/w to about 450% w/w, or from about 0.1% w/w to about 40% w/w, or from about 0.1% w/w to about 35% w/w, or from about 0.1% w/w to about 30% w/w, or from about 0.1% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 45% w/w, or from about 1% w/w to about 45% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 7% w/w, or from about 1% w/w to about 6% w/w, or from about 1% w/w to about 5% w/w, or from about 1% w/w to about 4% w/w, or from about 1% w/w to about 3% w/w, or from about 1% w/w to about 2% w/w, or from about 2% w/w to about 45% w/w, or from about 2% w/w to about 40% w/w, or from about 2% w/w to about 35% w/w, or from about 2% w/w to about 30% w/w, or from about 2% w/w to about 25% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the methods and/or kits disclosed herein, wherein the hydrogen peroxide is at a concentration of about 0.1% w/w, or about 0.5% w/w, or about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods and/or kits disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the methods and/or kits disclosed herein, wherein the first composition applied to the face of the subject comprises from about 1 gram to about 25 grams of *Spongilla*, and from about 1 mL to about 50 mL of aqueous hydrogen peroxide; or from about 1 gram to about 20 grams of *Spongilla* and from about 1 mL to about 50 mL of aqueous hydrogen peroxide; or from about 1 gram to about 15 grams of *Spongilla* and from about 1 mL to about 50 mL of aqueous hydrogen peroxide; or from about 1 gram to about 10 grams of *Spongilla* and from about 1 mL to about 50 mL of aqueous hydrogen peroxide; or from about 1 gram to about 9 grams of *Spongilla* and from about 1 mL to about 50 mL of aqueous hydrogen peroxide; or from about 1 gram to about 8 grams of *Spongilla* and from about 1 mL to about 50 mL of aqueous hydrogen peroxide; or from about 1 gram to about 7 grams of *Spongilla* and from about 1 mL to about 50 mL of aqueous hydrogen peroxide; or from about 1 gram to about 6 grams of *Spongilla* and from about 1 mL to about 50 mL of aqueous hydrogen peroxide; or from about 1 gram to about 5 grams of *Spongilla* and from about 1 mL to about 50 mL of aqueous hydrogen peroxide; or from about 1 gram to about 4 grams of *Spongilla* and from about 1 mL to about 50 mL of aqueous hydrogen peroxide; or from about 1 gram to about 3 grams of *Spongilla* and from about 1 mL to about 50 mL of aqueous hydrogen peroxide; or from about 1 gram to about 2 grams of *Spongilla* and from about 1 mL to about 50 mL of aqueous hydrogen peroxide; or from about 1 gram to about 20 grams of *Spongilla* and from about 1 mL to about 25 mL of aqueous hydrogen peroxide; or from about 1 gram to about 20 grams of *Spongilla* and from about 1 mL to about 20 mL of aqueous hydrogen peroxide; or from about 1 gram to about 20 grams of *Spongilla* and from about 1 mL to about 15 mL of aqueous hydrogen peroxide; or from about 1 gram to about 20 grams of *Spongilla* and from about 1 mL to about 10 mL of aqueous hydrogen peroxide; or from about 1 gram to about 20 grams of *Spongilla* and from about 1 mL to about 9 mL of aqueous hydrogen peroxide; or from about 1 gram to about 20 grams of *Spongilla* and from about 1 mL to about 8 mL of aqueous hydrogen peroxide; or from about 1 gram to about 20 grams of *Spongilla* and from about 1 mL to about 7 mL of aqueous hydrogen peroxide; or from about 1 gram to about 20 grams of *Spongilla* and from about 1 mL to about 6 mL of aqueous hydrogen peroxide; or from about 1 gram to about 20 grams of *Spongilla* and from about 1 mL to about 5 mL of aqueous hydrogen peroxide; or from about 1 gram to about 20 grams of *Spongilla* and from about 1 mL to about 4 mL of aqueous hydrogen peroxide; or from about 1 gram to about 20 grams of *Spongilla* and from about 1 mL to about 3 mL of aqueous hydrogen peroxide; or from about 1 gram to about 20 grams of *Spongilla* and from about 1 mL to about 2 mL of aqueous hydrogen peroxide; or from about 1 gram to about 10 grams of *Spongilla* and from about 1 mL to about 15 mL of aqueous hydrogen peroxide; or from about 2 grams to about 10 grams of *Spongilla* and from about 1 mL to about 15 mL of aqueous hydrogen peroxide; or from about 1 gram to about 10 grams of *Spongilla* and from about 1 mL to about 10 mL of aqueous hydrogen peroxide; or from about 1 gram to about 9 grams of *Spongilla* and from about 1 mL to about 10 mL of aqueous hydrogen peroxide; or from about 1 gram to about 8 grams of *Spongilla* and from about 1 mL to about 10 mL of aqueous hydrogen peroxide; or from about 1 gram to about 7 grams of *Spongilla* and from about 1 mL to about 10 mL of aqueous hydrogen peroxide; or from about 1 gram to about 6 grams of *Spongilla* and from about 1 mL to about 10 mL of aqueous hydrogen peroxide; or from about 1 gram to about 5 grams of *Spongilla* and from about 1 mL to about 10 mL of aqueous hydrogen peroxide; or from about 1 gram to about 4 grams of *Spongilla* and from about 1 mL to about 10 mL of aqueous hydrogen peroxide; or from about 1 gram to about 3 grams of *Spongilla* and from about 1 mL to about 10 mL of aqueous hydrogen peroxide; or from about 1 gram to about 2 grams of *Spongilla* and from about 1 mL to about 10 mL of aqueous hydrogen peroxide; or from about 1 gram to about 5 grams of *Spongilla* and from about 1 mL to about 10 mL of aqueous hydrogen peroxide; or from about 1 gram to about 5 grams of *Spongilla* and from about 1 mL to about 9 mL of aqueous hydrogen peroxide; or from about 1 gram to about 5 grams of *Spongilla* and from about 2 mL to about 10 mL of aqueous hydrogen peroxide; or from about 1 gram to about 4 grams of *Spongilla* and from about 1 mL to about 10 mL of aqueous hydrogen peroxide; or from about 1 gram to about 3 grams of *Spongilla* and from about 1 mL to about 10 mL of aqueous hydrogen peroxide; or about 1 gram of *Spongilla* and about 10 mL of aqueous hydrogen peroxide; or about 1 gram of *Spongilla* and about 9 mL of aqueous hydrogen peroxide; or about 1 gram of *Spongilla* and about 8 mL of aqueous hydrogen peroxide; or about 1 gram of *Spongilla* and about 7 mL of aqueous hydrogen peroxide; or about 1 gram of *Spongilla* and about 6 mL of aqueous hydrogen peroxide; or about 2 grams of *Spongilla* and about 10 mL of aqueous hydrogen peroxide; or about 2 grams of *Spongilla* and about 9 mL of aqueous hydrogen peroxide; or about 2 grams of *Spongilla* and about 8 mL of aqueous hydrogen peroxide; or about 2 grams of *Spongilla* and about 7 mL of aqueous hydrogen peroxide; or about 2 grams of *Spongilla* and about 6 mL of aqueous hydrogen peroxide; or about 2 grams of *Spongilla* and about 5 mL of aqueous hydrogen peroxide; or about 2 grams of *Spongilla* and about 4 mL of aqueous hydrogen peroxide; or about 2 grams of *Spongilla* and about 3 mL of aqueous hydrogen peroxide; or about 2 grams of *Spongilla* and about 2 mL of aqueous hydrogen peroxide; or about 2 grams of *Spongilla* and about 1 mL of aqueous hydrogen peroxide. In another aspect is provided any of the methods and/or kits disclosed herein, wherein the aqueous hydrogen peroxide is 3% hydrogen peroxide. In another aspect is provided any of the methods and/or kits disclosed herein, wherein the composition comprises about 2 gram of *Spongilla* and about 6 mL of 3% hydrogen peroxide.

In another aspect is provided any of the methods disclosed herein, wherein the subject washes the composition from the area of the skin treated following application. In another aspect is provided any of the methods disclosed herein, wherein the subject washes the composition from the area of the skin treated within about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 45 minutes, about 60 minutes, about 90 minutes, about 120 minutes, or about 180 minutes following application. In another aspect is provided any of the methods disclosed herein, wherein the subject washes the composition from the area of the skin treated about 15 minutes following application.

In one aspect is provided a method of treating a skin condition in a subject, comprising applying to the skin of the subject a composition comprising a first composition comprising *Spongilla*, and a second composition comprising one or more fluidizing agents, wherein said first composition comprises about 2 grams of *Spongilla*, said second composition comprises about 6 mL of 3% hydrogen peroxide, wherein the skin condition is acne vulgaris. In another aspect is provided any of the methods disclosed herein, wherein the skin condition is moderate acne vulgaris, severe acne vulgaris, facial acne vulgaris, moderate facial acne vulgaris, or severe acne vulgaris. In another aspect is provided any of the methods disclosed herein, wherein the composition is applied to the face of the subject. In another aspect is provided any of the methods disclosed herein, wherein the subject washes the composition from their face within 15 minutes following application. In another aspect is provided any of the methods disclosed herein, wherein the subject experiences a reduction in the total number of acne vulgaris lesions of about 10%, about 20%, about 30%, about 40%, about 50%, about 60%, about 70%, about 80%, about 90%, or about 99% following treatment compared to the number of acne vulgaris lesions experienced by the subject prior to treatment. In another aspect is provided any of the methods disclosed herein, wherein the subject experiences an improvement from baseline in the Investigator's Global Assessment (IGA) severity scale following treatment, or a one-grade improvement, or a two-grade improvement, or a three-grade improvement. In another aspect is provided any of the methods disclosed herein, wherein the subject has a score of 2 or less on the Investigator's Global Assessment (IGA) severity scale following treatment, or a score of 1 or less on the Investigator's Global Assessment (IGA) severity scale following treatment, a score of zero on the Investigator's Global Assessment (IGA) severity scale following treatment. In another aspect is provided any of the methods disclosed herein, wherein the subject experiences a decrease in the subject's total score in Dermatology Life Quality Index (DLQI) following treatment compared to the subject's score in Dermatology Life Quality Index (DLQI) prior to treatment, or a decrease of at least one point in the subject's total score in Dermatology Life Quality Index (DLQI) following treatment compared to the subject's score in Dermatology Life Quality Index (DLQI) prior to treatment, or a decrease of at least two points in the subject's total score in Dermatology Life Quality Index (DLQI) following treatment compared to the subject's score in Dermatology Life Quality Index (DLQI) prior to treatment, a decrease of at least three points in the subject's total score in Dermatology Life Quality Index (DLQI) following treatment compared to the subject's score in Dermatology Life Quality Index (DLQI) prior to treatment; or a decrease of at least four points in the subject's total score in Dermatology Life Quality Index (DLQI) following treatment compared to the subject's score in Dermatology Life Quality Index (DLQI) prior to treatment.

In one aspect is provided a method of treating a skin condition in a subject, comprising applying to the skin of the subject a composition comprising a first composition comprising *Spongilla*, and a second composition comprising one or more fluidizing agents, wherein said first composition comprises about 2 grams of *Spongilla*, said second composition comprises about 6 mL of 3% hydrogen peroxide, wherein the skin condition is acne vulgaris, and wherein the subject experiences a reduction in the total number of acne vulgaris lesions of about 10%, about 20%, about 30%, about 40%, about 50%, about 60%, about 70%, about 80%, about 90%, or about 99% following treatment. In another aspect, the skin condition is moderate acne vulgaris, severe acne vulgaris, facial acne vulgaris, moderate facial acne vulgaris, or severe acne vulgaris. In another aspect, the composition is applied to the face of the subject.

In one aspect is provided a method of treating a skin condition in a subject, comprising applying to the skin of the subject a composition comprising a first composition comprising *Spongilla*, and a second composition comprising one or more fluidizing agents, wherein said first composition comprises about 2 grams of *Spongilla*, said second composition comprises about 6 mL of 3% hydrogen peroxide, wherein the skin condition is acne vulgaris, and wherein the subject experiences an improvement from baseline in the Investigator's Global Assessment (IGA) severity scale following treatment. In another aspect, the subject experiences an improvement from baseline in the Investigator's Global Assessment (IGA) severity scale following treatment, or a one-grade improvement, or a two-grade improvement, or a three-grade improvement. In another aspect, the subject has a score of 2 or less on the Investigator's Global Assessment (IGA) severity scale following treatment, or a score of 1 or less on the Investigator's Global Assessment (IGA) severity scale following treatment, a score of zero on the Investigator's Global Assessment (IGA) severity scale following treatment In another aspect, the skin condition is moderate acne vulgaris, severe acne vulgaris, facial acne vulgaris, moderate facial acne vulgaris, or severe acne vulgaris. In another aspect, the composition is applied to the face of the subject.

In one aspect is provided a method of treating a skin condition in a subject, comprising applying to the skin of the subject a composition comprising a first composition comprising *Spongilla*, and a second composition comprising one or more fluidizing agents, wherein said first composition comprises about 2 grams of *Spongilla*, said second composition comprises about 6 mL of 3% hydrogen peroxide, wherein the skin condition is acne vulgaris, and wherein the subject experiences a decrease in the total score in Dermatology Life Quality Index (DLQI) following treatment compared to the subject's score in Dermatology Life Quality Index (DLQI) prior to treatment. In another aspect, the subject experiences a decrease of at least one point in the subject's total score in Dermatology Life Quality Index (DLQI) following treatment compared to the subject's score in Dermatology Life Quality Index (DLQI) prior to treatment, or a decrease of at least two points in the subject's total score in Dermatology Life Quality Index (DLQI) following treatment compared to the subject's score in Dermatology Life Quality Index (DLQI) prior to treatment, a decrease of at least three points in the subject's total score in Dermatology Life Quality Index (DLQI) following treatment compared to the subject's score in Dermatology Life Quality Index (DLQI) prior to treatment; a decrease of at least four points in the subject's total score in Dermatology Life Quality Index (DLQI) following treatment compared to the subject's score in Dermatology Life Quality Index (DLQI) prior to treatment In another aspect is provided any of the methods and/or kits disclosed herein, wherein the first composition comprises *Spongilla* in the form of a powder. Materials comprising *Spongilla* may be prepared in powdered form having particles of substantially the same size, using techniques known to those having ordinary skill in the art, such as grinding and sieving. In another aspect is provided any of the methods and/or kits disclosed herein, wherein the *Spongilla* is in the form of a powder comprising particles that are substantially uniform in size. In another aspect is provided any of the methods and/or kits disclosed herein, wherein not less than about 50% of the particles comprising the *Spongilla* powder pass through a US 70-mesh screen. In another aspect is provided any of the methods and/or kits disclosed herein, wherein not less than about 60%, or about 70%, or about 75%, or about 80%, or about 85%, or about 90%, or about 95%, or about 96%, or about 97%, or about 98%, or about 99% of the particles comprising the *Spongilla* powder pass through a US 70-mesh screen. In another aspect is provided any of the methods and/or kits disclosed herein, wherein not less than about 95%, or about 96%, or about 97%, or about 98%, or about 99% of the particles comprising the *Spongilla* powder pass through a US 70-mesh screen. In another aspect is provided any of the methods and/or kits disclosed herein, wherein not less than about 95% of the particles comprising the *Spongilla* powder pass through a US 70-mesh screen. In another aspect is provided any of the methods and/or kits disclosed herein, wherein not less than about 96% of the particles comprising the *Spongilla* powder pass through a US 70-mesh screen. In another aspect is provided any of the methods and/or kits disclosed herein, wherein not less than about 97% of the particles comprising the *Spongilla* powder pass through a US 70-mesh screen. In another aspect is provided any of the methods and/or kits disclosed herein, wherein not less than about 98% of the particles comprising the *Spongilla* powder pass through a US 70-mesh screen. In another aspect is provided any of the methods and/or kits disclosed herein, wherein not less than about 99% of the particles comprising the *Spongilla* powder pass through a US 70-mesh screen. The particles of *Spongilla* may be manufactured or produced from *Spongilla* materials that are harvested by procedures known to those of ordinary skill in the art, such as determining the appropriate harvest period, removal of foreign materials, drying, milling and grinding using equipment known to those of ordinary skill in the art.

In another aspect is provided any of the methods and/or kits disclosed herein, wherein the particles comprising the *Spongilla* powder have an average length of from about 50 μm to about 500 μm. In another aspect is provided any of the methods and/or kits disclosed herein, wherein the particles comprising the *Spongilla* powder have an average length of from about 50 μm to about 400 μm, or from about 50 μm to about 350 μm, or from about 50 μm to about 300 μm, or from about 50 μm to about 250 μm, or from about 50 μm to about 200 μm, or from about 75 μm to about 500 μm, or from about 75 μm to about 450 μm, or from about 80 μm to about 450 μm, or from about 80 μm to about 400 μm, or from about 85 μm to about 450 μm, or from about 85 μm to about 400 μm, or from about 90 μm to about 450 μm, or from about 90 μm to about 400 μm, or from about 90 μm to about 350 μm, or from about 100 μm to about 450 μm, or from about 100 μm to about 400 μm, or from about 100 μm to about 350 μm, or from about 100 μm to about 300 μm, or from about 100 μm to about 250 μm, or from about 100 μm to about 200 μm, or from about 150 μm to about 500 μm, or from about 100 μm to about 450 μm, or from about 150 μm to about 400 μm, or from about 150 μm to about 350 μm, or from about 150 μm to about 350 μm, or from about 150 μm to about 300 μm, or from about 150 μm to about 250 μm, or from about 150 μm to about 200 μm, or from about 175 μm to about 450 μm, or from about 175 μm to about 400 μm, or from about 175 μm to about 350 μm, or from about 175 μm to about 300 μm, or from about 175 μm to about 250 μm, or from about 175 μm to about 200 μm. In another aspect is provided any of the methods and/or kits disclosed herein, wherein the particles comprising the *Spongilla* powder have an average length of about 50 μm, or about 75 μm, or about 80 μm, or about 85 μm, or about 90 μm, or about 100 μm, or about 125 μm, or about 150 µm, or about 175 µm, or about 200 µm, or about 225 µm, or about 250 µm, or about 300 µm, or about 350 µm, or about 400 µm, or about 450 µm, or about 500 µm. In another aspect is provided any of the methods and/or kits disclosed herein, wherein the particles comprising the *Spongilla* powder have an average length of about 200 µm. The particles comprising the *Spongilla* powder may be manufactured or produced from *Spongilla* materials that are harvested by procedures known to those of ordinary skill in the art, such as milling and grinding using equipment known to those of ordinary skill in the art. The average length of particles comprising the *Spongilla* powder may be measured using analytical methods and/or kits known to those of ordinary skill in the art, such as, for example, scanning electron microscopy (SEM) and sieve analysis. Sieve analysis may also be used to determine the particle size distribution of the particles comprising the *Spongilla* powder.

In another aspect is provided any of the methods and/or kits disclosed herein, wherein the particles comprising the *Spongilla* powder have an average diameter of from about 5 µm to about 50 µm. In another aspect is provided any of the methods and/or kits disclosed herein, wherein the particles comprising the *Spongilla* powder have an average diameter of from about 5 µm to about 45 µm, or from about 5 µm to about 40 µm, from about 5 µm to about 35 µm, from about 5 µm to about 30 µm, from about 5 µm to about 25 µm, from about 5 µm to about 20 µm, from about 10 µm to about 45 µm, from about 10 µm to about 40 µm, from about 10 µm to about 35 µm, from about 10 µm to about 30 µm, from about 10 µm to about 25 µm, from about 10 µm to about 20 µm. In another aspect is provided any of the methods and/or kits disclosed herein, wherein the particles comprising the *Spongilla* powder have an average diameter of about 5 µm, or about 10 µm, or about 15 µm, or about 20 µm, or about 25 µm, or about 30 µm, or about 35 µm, or about 40 µm, or about 45 µm, or about 50 µm. The particles comprising the *Spongilla* powder may be manufactured or produced from *Spongilla* materials that are harvested by procedures known to those of ordinary skill in the art, such as milling and grinding using equipment known to those of ordinary skill in the art. The average diameter of particles comprising the *Spongilla* powder may be measured using analytical methods and/or kits known to those of ordinary skill in the art, such as, for example, scanning electron microscopy (SEM) and sieve analysis. Sieve analysis may also be used to determine the particle size distribution of the particles comprising the *Spongilla* powder In another aspect is provided any of the methods and/or kits disclosed herein, wherein the particles comprising the *Spongilla* powder have an aspect ratio of from about 1 to about 100. In another aspect is provided any of the methods and/or kits disclosed herein, wherein the particles comprising the *Spongilla* powder have an aspect ratio of from about 1 to about 75, or from about 1 to about 50, or from about 1 to about 25, or from about 1 to about 20, or from about 1 to about 15, or from about 5 to about 100, or from about 5 to about 75, or from about 5 to about 50, or from about 5 to about 40, or from about 5 to about 35, or from about 5 to about 30, or from about 5 to about 25, or from about 5 to about 20, or from about 5 to about 15, or from about 7 to about 50, or from about 7 to about 45, or from about 7 to about 40, or from about 7 to about 35, or from about 7 to about 30, or from about 7 to about 25, or from about 10 to about 50, or from about 10 to about 45, or from about 10 to about 40, or from about 10 to about 35, or from about 10 to about 30, or from about 10 to about 25, or from about 10 to about 15. In another aspect is provided any of the methods and/or kits disclosed herein, wherein the particles comprising the *Spongilla* powder have an aspect ratio of about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30, or about 35, or about 40, or about 45, or about 50, or about 75, or about 100. The particles comprising the *Spongilla* powder may be manufactured or produced from *Spongilla* materials that are harvested by procedures known to those of ordinary skill in the art, such as milling and grinding using equipment known to those of ordinary skill in the art. The aspect ratio of particles comprising the *Spongilla* powder may be measured using analytical methods known to those of ordinary skill in the art, such as, for example, scanning electron microscopy (SEM) and sieve analysis. Sieve analysis may also be used to determine the particle size distribution of the particles comprising the *Spongilla* powder Materials comprising *Spongilla* may be processed and dried, using techniques known to those having ordinary skill in the art, such as the use of drying ovens, to provide materials having a desired residual moisture content. In another aspect is provided any of the methods and/or kits disclosed herein, wherein the first composition comprising *Spongilla* has a residual moisture content of not more than about 20%. In another aspect is provided any of the methods and/or kits disclosed herein, wherein the first composition has a residual moisture content of not more than about 15%, or not more than about 10%, or not more than about 9%, or not more than about 8%, or not more than about 7%, or not more than about 6%, or not more than about 5%, or not more than about 4%, or not more than about 3%, or not more than about 2%, or not more than 1%. In another aspect is provided any of the methods and/or kits disclosed herein, wherein the first composition has a residual moisture content of not more than about 5%. In another aspect is provided any of the methods and/or kits disclosed herein, wherein the first composition has a residual moisture content of not more than about 4%. In another aspect is provided any of the methods and/or kits disclosed herein, wherein the first composition has a residual moisture content of not more than about 3%. In another aspect is provided any of the methods and/or kits disclosed herein, wherein the first composition has a residual moisture content of not more than about 2%. In another aspect is provided any of the methods and/or kits disclosed herein, wherein the first composition has a residual moisture content of not more than about 1%. The moisture content of the *Spongilla* materials can be reduced by heating the raw *Spongilla* materials using methods and/or kits known to those of ordinary skill in the art, such as by open-air drying, or by use of a conventional oven dryer or a vacuum dryer, using equipment known to those of ordinary skill in the art. For example, raw *Spongilla* materials may be placed into a tray and heated in a drying oven at a temperature range from about 30° C. to about 200° C., for example to about 70° C., for a period of time necessary to reduce the residual moisture content to the desired level. The level of residual moisture of the materials may be measured using methods known to those of ordinary skill in the art such as those described in the United States Pharmacopeia methods USP <731> (Loss on Drying) and USP <921> (Water Determination).

Materials comprising *Spongilla* may be treated in order to reduce the bioburden, such as aerobic and anaerobic microbes, yeast and mold, Coliform bacteria, *Salmonella*,

*Pseudomonas aeruginosa*, and *Staphylococcus aureus*, of the materials prior to their packaging and use, such as by use of heat treatment or irradiation, such as the use of gamma irradiation.

In another aspect is provided any of the methods and/or kits disclosed herein, wherein the first composition has a combined aerobic and anaerobic microbial content of not more than about $25 \times 10^4$ colony-forming units per gram (CFU/g). In another aspect is provided any of the methods and/or kits disclosed herein, wherein the first composition has a combined aerobic and anaerobic microbial content of not more than about $10 \times 10^4$ CFU/g, or not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a combined aerobic and anaerobic microbial content of not more than about 1,000 CFU/g. In another aspect is provided any of the methods and/or kits disclosed herein, wherein the first composition has a combined aerobic and anaerobic microbial content of not more than about 750 CFU/g. In another aspect is provided any of the methods and/or kits disclosed herein, wherein the first composition has a combined aerobic and anaerobic microbial content of not more than about 500 CFU/g. In another aspect is provided any of the methods and/or kits disclosed herein, wherein the first composition has a combined aerobic and anaerobic microbial content of not more than about 250 CFU/g. In another aspect is provided any of the methods and/or kits disclosed herein, wherein the first composition has a combined aerobic and anaerobic microbial content of not more than about 200 CFU/g. In another aspect is provided any of the methods and/or kits disclosed herein, wherein the first composition has a combined aerobic and anaerobic microbial content of not more than about 150 CFU/g. In another aspect is provided any of the methods and/or kits disclosed herein, wherein the first composition has a combined aerobic and anaerobic microbial content of not more than about 100 CFU/g. In another aspect is provided any of the methods and/or kits disclosed herein, wherein the first composition has a combined aerobic and anaerobic microbial content of not more than about 75 CFU/g. In another aspect is provided any of the methods and/or kits disclosed herein, wherein the first composition has a combined aerobic and anaerobic microbial content of not more than about 50 CFU/g. In another aspect is provided any of the methods and/or kits disclosed herein, wherein the first composition has a combined aerobic and anaerobic microbial content of not more than about 25 CFU/g. In another aspect is provided any of the methods and/or kits disclosed herein, wherein the first composition has a combined aerobic and anaerobic microbial content of not more than about 20 CFU/g. In another aspect is provided any of the methods and/or kits disclosed herein, wherein the first composition has a combined aerobic and anaerobic microbial content of not more than about 10 CFU/g. In another aspect is provided any of the methods and/or kits disclosed herein, wherein the first composition has a combined aerobic and anaerobic microbial content of not more than about 1 CFU/g. In another aspect is provided any of the methods and/or kits disclosed herein, wherein the first composition has a combined aerobic and anaerobic microbial content of not more than about $1 \times 10^3$ CFU/g. The combined aerobic and anaerobic microbial content of the *Spongilla* materials may be reduced by physical or chemical methods and/or kits known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The combined aerobic and anaerobic microbial content of the *Spongilla* materials may be measured by methods known to those of ordinary skill in the art, such as those described in the United States Pharmacopeia method USP <61> (Microbial Enumeration Tests).

In another aspect is provided any of the methods and/or kits disclosed herein, wherein the first composition comprising *Spongilla* has a combined yeast and mold content of not more than about $25 \times 10^4$ colony-forming units per gram (CFU/g). In another aspect is provided any of the methods and/or kits disclosed herein, wherein the first composition has a combined yeast and mold content of not more than about or not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a combined yeast and mold content of not more than about 1,000 CFU/g. In another aspect is provided any of the methods and/or kits disclosed herein, wherein the first composition has a combined yeast and mold content of not more than about 750 CFU/g. In another aspect is provided any of the methods and/or kits disclosed herein, wherein the first composition has a combined yeast and mold content of not more than about 500 CFU/g. In another aspect is provided any of the methods and/or kits disclosed herein, wherein the first composition has a combined yeast and mold content of not more than about 250 CFU/g. In another aspect is provided any of the methods and/or kits disclosed herein, wherein the first composition has a combined yeast and mold content of not more than about 200 CFU/g. In another aspect is provided any of the methods and/or kits disclosed herein, wherein the first composition has a combined yeast and mold content of not more than about 150 CFU/g. In another aspect is provided any of the methods and/or kits disclosed herein, wherein the first composition has a combined yeast and mold content of not more than about 100 CFU/g. In another aspect is provided any of the methods and/or kits disclosed herein, wherein the first composition has a combined yeast and mold content of not more than about 75

CFU/g. In another aspect is provided any of the methods and/or kits disclosed herein, wherein the first composition has a combined yeast and mold content of not more than about 50 CFU/g. In another aspect is provided any of the methods and/or kits disclosed herein, wherein the first composition has a combined yeast and mold content of not more than about 25 CFU/g. In another aspect is provided any of the methods and/or kits disclosed herein, wherein the first composition has a combined yeast and mold content of not more than about 20 CFU/g. In another aspect is provided any of the methods and/or kits disclosed herein, wherein the first composition has a combined yeast and mold content of not more than about 10 CFU/g. In another aspect is provided any of the methods and/or kits disclosed herein, wherein the first composition has a combined yeast and mold content of not more than about 1 CFU/g. In another aspect is provided any of the methods and/or kits disclosed herein, wherein the first composition has a combined yeast and mold content of not more than about $1 \times 10^3$ CFU/g. The combined yeast and mold content of the *Spongilla* materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The combined yeast and mold content of the *Spongilla* materials may be measured by methods known to those of ordinary skill in the art, such as those described in the United States Pharmacopeia method USP <61> (Microbial Enumeration Tests).

In another aspect is provided any of the methods and/or kits disclosed herein, wherein the amount of Coliform bacteria in the first composition is not more than about $25 \times 10^4$ colony-forming units per gram (CFU/g). In another aspect is provided any of the methods and/or kits disclosed herein, wherein the amount of Coliform bacteria in the first composition is not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a Coliform bacteria content of not more than about 1,000 CFU/g. In another aspect is provided any of the methods and/or kits disclosed herein, wherein the first composition has a Coliform bacteria content of not more than about 750 CFU/g. In another aspect is provided any of the methods and/or kits disclosed herein, wherein the first composition has a Coliform bacteria content of not more than about 500 CFU/g. In another aspect is provided any of the methods and/or kits disclosed herein, wherein the first composition has a Coliform bacteria content of not more than about 250 CFU/g. In another aspect is provided any of the methods and/or kits disclosed herein, wherein the first composition has a Coliform bacteria content of not more than about 200 CFU/g. In another aspect is provided any of the methods and/or kits disclosed herein, wherein the first composition has a Coliform bacteria content of not more than about 150 CFU/g. In another aspect is provided any of the methods and/or kits disclosed herein, wherein the first composition has a Coliform bacteria content of not more than about 100 CFU/g. In another aspect is provided any of the methods and/or kits disclosed herein, wherein the first composition has a Coliform bacteria content of not more than about 75 CFU/g. In another aspect is provided any of the methods and/or kits disclosed herein, wherein the first composition has a Coliform bacteria content of not more than about 50 CFU/g. In another aspect is provided any of the methods and/or kits disclosed herein, wherein the first composition has a Coliform bacteria content of not more than about 25 CFU/g. In another aspect is provided any of the methods and/or kits disclosed herein, wherein the first composition has a Coliform bacteria content of not more than about 20 CFU/g. In another aspect is provided any of the methods and/or kits disclosed herein, wherein the first composition has a Coliform bacteria content of not more than about 10 CFU/g. In another aspect is provided any of the methods and/or kits disclosed herein, wherein the first composition has a Coliform bacteria content of not more than about 1 CFU/g. In another aspect is provided any of the methods and/or kits disclosed herein, wherein the first composition has a Coliform bacteria content of not more than about $1 \times 10^3$ CFU/g. In another aspect is provided any of the methods and/or kits disclosed herein, wherein the first composition has no detectable Coliform bacterial content. The Coliform bacteria content of the *Spongilla* materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The Coliform bacteria content of the *Spongilla* materials may be measured by methods known to those of ordinary skill in the art, such as those described in the United States Pharmacopeia method USP <62> (Tests for Specified Microorganisms).

In another aspect is provided any of the methods and/or kits disclosed herein, wherein the amount of *Salmonella* in the first composition is not more than about $25 \times 10^4$ colony-forming units per gram (CFU/g). In another aspect is provided any of the methods and/or kits disclosed herein, wherein the amount of *Salmonella* in the first composition is not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a *Salmonella* content of not more than about 1,000 CFU/g. In another aspect is provided any of the methods and/or kits disclosed herein, wherein the first composition has a *Salmonella* content of not more than about 750 CFU/g. In another aspect is provided any of the methods and/or kits disclosed herein, wherein the first composition has a *Salmonella* content of not more than about 500 CFU/g. In another aspect is provided any of the methods and/or kits disclosed herein, wherein the first composition has a *Salmonella* content of not more than about 250 CFU/g. In another aspect is provided any of the methods and/or kits disclosed herein, wherein the first composition has a *Salmonella* content of not more than about 200 CFU/g. In another aspect is provided any of the methods and/or kits disclosed herein, wherein the first composition has a *Salmonella* content of not more than about 150 CFU/g. In another aspect is provided any of the methods and/or kits disclosed herein, wherein the first composition has a *Salmonella* content of not more than about 100 CFU/g. In another aspect is provided any of the methods and/or kits disclosed herein, wherein the first composition has a *Salmonella* content of not more than about 75 CFU/g. In another aspect is provided any of the methods and/or kits disclosed herein, wherein the first composition has a *Salmonella* content of not more than about 50 CFU/g. In another aspect is provided any of the methods and/or kits disclosed herein, wherein the first composition has a *Salmonella* content of not more than about 25 CFU/g. In another aspect is provided any of the methods and/or kits disclosed herein, wherein the first composition has a *Salmonella* content of not more than about 20 CFU/g. In another aspect is provided any of the methods and/or kits disclosed herein, wherein the first composition has a *Salmonella* content of not more than about 10 CFU/g. In another aspect is provided any of the methods and/or kits disclosed herein, wherein the first composition has a *Salmonella* content of not more than about 1 CFU/g. In another aspect is provided any of the methods and/or kits disclosed herein, wherein the amount of *Salmonella* in the first composition is not more than about $1 \times 10^3$ CFU/g. In another aspect is provided any of the methods and/or kits disclosed herein, wherein the first composition has no detectable *Salmonella* content. The *Salmonella* content of the *Spongilla* materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Salmonella* content of the *Spongilla* materials may be measured by methods known to those of ordinary skill in the art, such as those described in the United States Pharmacopeia method USP <62> (Tests for Specified Microorganisms).

In another aspect is provided any of the methods and/or kits disclosed herein, wherein the amount of *Pseudomonas aeruginosa* bacteria in the first composition is not more than about $25 \times 10^4$ colony-forming units per gram (CFU/g). In another aspect is provided any of the methods and/or kits disclosed herein, wherein the amount of *Pseudomonas aeruginosa* bacteria in the first composition is not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a *Pseudomonas aeruginosa* bacteria content of not more than about 1,000 CFU/g. In another aspect is provided any of the methods and/or kits disclosed herein, wherein the first composition has a *Pseudomonas aeruginosa* bacteria content of not more than about 750 CFU/g. In another aspect is provided any of the methods and/or kits disclosed herein, wherein the first composition has a *Pseudomonas aeruginosa* bacteria content of not more than about 500 CFU/g. In another aspect is provided any of the methods and/or kits disclosed herein, wherein the first composition has a *Pseudomonas aeruginosa* bacteria content of not more than about 250 CFU/g. In another aspect is provided any of the methods and/or kits disclosed herein, wherein the first composition has a *Pseudomonas aeruginosa* bacteria content of not more than about 200 CFU/g. In another aspect is provided any of the methods and/or kits disclosed herein, wherein the first composition has a *Pseudomonas aeruginosa* bacteria content of not more than about 150 CFU/g. In another aspect is provided any of the methods and/or kits disclosed herein, wherein the first composition has a *Pseudomonas aeruginosa* bacteria content of not more than about 100 CFU/g. In another aspect is provided any of the methods and/or kits disclosed herein, wherein the first composition has a *Pseudomonas aeruginosa* bacteria content of not more than about 75 CFU/g. In another aspect is provided any of the methods and/or kits disclosed herein, wherein the first composition has a *Pseudomonas aeruginosa* bacteria content of not more than about 50 CFU/g. In another aspect is provided any of the methods and/or kits disclosed herein, wherein the first composition has a *Pseudomonas aeruginosa* bacteria content of not more than about 25 CFU/g. In another aspect is provided any of the methods and/or kits disclosed herein, wherein the first composition has a *Pseudomonas aeruginosa* bacteria content of not more than about 20 CFU/g. In another aspect is provided any of the methods and/or kits disclosed herein, wherein the first composition has a *Pseudomonas aeruginosa* bacteria content of not more than about 10 CFU/g. In another aspect is provided any of the methods and/or kits disclosed herein, wherein the first composition has a *Pseudomonas aeruginosa* bacteria content of not more than about 1 CFU/g. In another aspect is provided any of the methods and/or kits disclosed herein, wherein the amount of *Pseudomonas aeruginosa* bacteria in the first composition is not more than about $1 \times 10^3$ CFU/g. In another aspect is provided any of the methods and/or kits disclosed herein, wherein the first composition has no detectable *Pseudomonas aeruginosa* bacteria content. The *Pseudomonas aeruginosa* bacteria content of the *Spongilla* materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Pseudomonas aeruginosa* bacteria content of the *Spongilla* materials may be measured by methods known to those of ordinary skill in the art, such as those described in the United States Pharmacopeia method USP <62> (Tests for Specified Microorganisms).

In another aspect is provided any of the methods and/or kits disclosed herein, wherein the amount of *Staphylococcus aureus* bacteria in the first composition is not more than about $25 \times 10^4$ colony-forming units per gram (CFU/g). In another aspect is provided any of the methods and/or kits disclosed herein, wherein the amount of *Staphylococcus aureus* bacteria in the first composition is not more than about $5 \times 10^4$ CFU/g, or not more than about $1 \times 10^4$ CFU/g, or not more than about $5 \times 10^3$ CFU/g, or not more than about $1 \times 10^4$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods and/or kits disclosed herein, wherein the first composition has a *Staphylococcus aureus* bacteria content of not more than about 1,000 CFU/g. In another aspect is provided any of the methods and/or kits disclosed herein, wherein the first composition has a *Staphylococcus aureus* bacteria content of not more than about 750 CFU/g. In another aspect is provided any of the methods and/or kits disclosed herein, wherein the first composition has a *Staphylococcus aureus* bacteria content of not more than about 500 CFU/g. In another aspect is provided any of the methods and/or kits disclosed herein, wherein the first composition has a *Staphylococcus aureus* bacteria content of not more than about 250 CFU/g. In another aspect is provided any of the methods and/or kits disclosed herein, wherein the first composition has a *Staphylococcus aureus* bacteria content of not more than about 200 CFU/g. In another aspect is provided any of the methods and/or kits disclosed herein, wherein the first composition has a *Staphylococcus aureus* bacteria content of not more than about 150 CFU/g. In another aspect is provided any of the methods and/or kits disclosed herein, wherein the first composition has a *Staphylococcus aureus* bacteria content of not more than about 100 CFU/g. In another aspect is provided any of the methods and/or kits disclosed herein, wherein the first composition has a *Staphylococcus aureus* bacteria content of not more than about 75 CFU/g. In another aspect is provided any of the methods and/or kits disclosed herein, wherein the first composition has a *Staphylococcus aureus* bacteria content of not more than about 50 CFU/g. In another aspect is provided any of the methods and/or kits disclosed herein, wherein the first composition has a *Staphylococcus aureus* bacteria content of not more than about 25 CFU/g. In another aspect is provided any of the methods and/or kits disclosed herein, wherein the first composition has a *Staphylococcus aureus* bacteria content of not more than about 20 CFU/g. In another aspect is provided any of the methods and/or kits disclosed herein, wherein the first composition has a *Staphylococcus aureus* bacteria content of not more than about 10 CFU/g. In another aspect is provided any of the methods and/or kits disclosed herein, wherein the first composition has a *Staphylococcus aureus* bacteria content of not more than about 1 CFU/g. In another aspect is provided any of the methods and/or kits disclosed herein, wherein the amount of *Staphylococcus aureus* bacteria in the first composition is not more than about $1 \times 10^3$ CFU/g. In another aspect is provided any of the methods and/or kits disclosed herein, wherein the first composition has no detectable *Staphylococcus aureus* bacteria content. The *Staphylococcus aureus* bacteria content of the *Spongilla* materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Staphylococcus aureus* bacteria content of the *Spongilla* materials may be measured by methods known to those of ordinary skill in the art, such as those described in the United States Pharmacopeia method USP <62> (Tests for Specified Microorganisms).

In another aspect is provided any of the methods and/or kits disclosed herein, wherein the first composition is packaged prior to use. In another aspect is provided any of the methods and/or kits disclosed herein, wherein the first composition is prepared by heating to at least about 70° C. prior to being packaged in order to reduce the bioburden. In another aspect is provided any of the methods and/or kits disclosed herein, wherein the first composition is prepared by heating to at least about 50° C., or at least about 60° C., or at least about 75° C., or at least about 80° C., or at least about 85° C., or at least about 90° C., or at least about 100° C., or at least about 110° C., or at least about 115° C., or at least about 120° C., or at least about 125° C., or at least about 130° C., or at least about 135° C., or at least about 140° C., or at least about 150° C., or at least about 160° C., or at least about 170° C., or at least about 180° C., or at least about 190° C., or at least about 200° C. prior to being packaged.

In another aspect is provided any of the methods and/or kits disclosed herein, wherein the first composition was packaged prior to use. In another aspect is provided any of the methods and/or kits disclosed herein, wherein the first composition was prepared by heating to at least about 70° C. prior to being packaged in order to reduce the bioburden. In another aspect is provided any of the methods and/or kits disclosed herein, wherein the first composition was prepared by heating to at least about 50° C., or at least about 60° C., or at least about 75° C., or at least about 80° C., or at least about 85° C., or at least about 90° C., or at least about 100° C., or at least about 110° C., or at least about 115° C., or at least about 120° C., or at least about 125° C., or at least about 130° C., or at least about 135° C., or at least about 140° C., or at least about 150° C., or at least about 160° C., or at least about 170° C., or at least about 180° C., or at least about 190° C., or at least about 200° C. prior to being packaged.

In another aspect is provided any of the methods and/or kits disclosed herein, wherein the first composition comprising *Spongilla* is heated to at least about 70° C. for at least about 5 minutes prior being packaged. In another aspect is provided any of the methods and/or kits disclosed herein, wherein the first composition is heated to at least about 70° C. for at least about 10 minutes, or at least about 15 minutes, or at least about 20 minutes, or at least about 25 minutes, or at least about 30 minutes, or at least about 35 minutes, or at least about 40 minutes, or at least about 45 minutes, or at least about 50 minutes, or at least about 55 minutes, or at least about 60 minutes, or at least about 75 minutes, or at least about 90 minutes, or at least about 120 minutes, or at least about 180 minutes, or at least about 4 hours, or at least about 5 hours, or at least about 6 hours, or at least about 7 hours, or at least about 8 hours, or at least about 9 hours, or at least about 10 hours, or at least about 11 hours, or at least about 12 hours, or at least about 24 hours prior being packaged.

In another aspect is provided any of the methods and/or kits disclosed herein, wherein the first composition comprising *Spongilla* was heated to at least about 70° C. for at least about 5 minutes prior being packaged. In another aspect is provided any of the methods and/or kits disclosed herein, wherein the first composition was heated to at least about 70° C. for at least about 10 minutes, or at least about 15 minutes, or at least about 20 minutes, or at least about 25 minutes, or at least about 30 minutes, or at least about 35 minutes, or at least about 40 minutes, or at least about 45 minutes, or at least about 50 minutes, or at least about 55 minutes, or at least about 60 minutes, or at least about 75 minutes, or at least about 90 minutes, or at least about 120 minutes, or at least about 180 minutes, or at least about 4 hours, or at least about 5 hours, or at least about 6 hours, or at least about 7 hours, or at least about 8 hours, or at least about 9 hours, or at least about 10 hours, or at least about 11 hours, or at least about 12 hours, or at least about 24 hours prior being packaged.

In another aspect is provided any of the methods and/or kits disclosed herein, wherein the first composition comprising *Spongilla* is or was prepared by treating with ionizing radiation, such as gamma radiation, prior to being packaged or after packaging. For example, gamma irradiation may be performed on the raw *Spongilla* material prior to grinding to reduce the particle size, following grinding to reduce the particle size, the materials packaged in bulk and or the materials following packaging in unit dose containers. The materials may be treated with ionizing radiation, such as gamma radiation, using methods and/or kits and equipment known to those of ordinary skill in the art, such as gamma irradiators or electron beam irradiators. In another aspect is provided any of the methods and/or kits disclosed herein, wherein the first composition is prepared by treating with ionizing radiation, such as gamma radiation, to deliver an absorbed radiation dose between about 1 kGy and about 50 kGy prior to being packaged. In another aspect is provided any of the methods and/or kits disclosed herein, wherein the first composition is prepared by treating with ionizing radiation, such as gamma radiation, to deliver an absorbed radiation dose between about 1 kGy and about 45 kGy, or between about 1 kGy and about 40 kGy, between about 1 kGy and about 35 kGy, between about 1 kGy and about 30 kGy, or between about 1 kGy and about 25 kGy or between about 5 kGy and about 50 kGy, or between about 5 kGy and about 45 kGy, or between about 5 kGy and about 40 kGy, or between about 5 kGy and about 35 kGy, or between about 5 kGy and about 30 kGy, or between about 5 kGy and about 25 kGy, or between about 10 kGy and about 50 kGy, or between about 10 kGy and about 45 kGy, or between about 10 kGy and about 40 kGy, or between about 10 kGy and about 35 kGy, or between about 10 kGy and about 30 kGy, or between about 10 kGy and about 25 kGy, or between about 15 kGy and about 50 kGy, or between about 15 kGy and about 45 kGy, or between about 15 kGy and about 40 kGy, or between about 15 kGy and about 35 kGy, or between about 15 kGy and about 30 kGy, or between about 15 kGy and about 25 kGy. In another aspect is provided any of the methods and/or kits disclosed herein, wherein the first composition is prepared by treating with ionizing radiation, such as gamma radiation, to deliver an absorbed radiation dose of about 1 kGy, or about 5 kGy, or about 10 kGy, 11 kGy, or about 12 kGy, or about 13 kGy, or about 14 kGy, or about 15 kGy, or about 16 kGy, or about 17 kGy, or about 18 kGy, or about 19 kGy, or about 20 kGy, or about 21 kGy, or about 22 kGy, or about 23 kGy, or about 24 kGy, or about 25 kGy, or about 26 kGy, or about 27 kGy, or about 28 kGy, or about 29 kGy, or about 30 kGy, or about 31 kGy, or about 32 kGy, or about 33 kGy, or about 34 kGy, or about 35 kGy, or about 36 kGy, or about 37 kGy, or about 38 kGy, or about 39 kGy, or about 40 kGy, or about 41 kGy, or about 42 kGy, or about 43 kGy, or about 44 kGy, or about 45 kGy, or about 46 kGy, or about 47 kGy, or about 48 kGy, or about 49 kGy, or about 50 kGy.

In another aspect is provided any of the methods disclosed herein, wherein the first composition is applied to the skin of the subject in the form of a paste. In another aspect is provided any of the methods disclosed herein, wherein the paste further comprises water or saline.

In another aspect is provided any of the methods and/or kits disclosed herein, wherein the second composition comprises an aqueous solution comprising hydrogen peroxide. In another aspect is provided any of the methods and/or kits disclosed herein, wherein the hydrogen peroxide is at a concentration of from about 0.1% w/w to about 50% w/w, or from about 0.1% w/w to about 45% w/w, or from about 0.1% w/w to about 40% w/w, or from about 0.1% w/w to about 35% w/w, or from about 0.1% w/w to about 30% w/w, or from about 0.1% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 450% w/w, or from about 1% w/w to about 450% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 8% w/w, or from about 1% w/w to about 7% w/w, or from about 1% w/w to about 6% w/w, or from about 1% w/w to about 50% w/w, or from about 1% w/w to about 4% w/w, or from about 1% w/w to about 3% w/w, or from about 1% w/w to about 2% w/w, or from about 2% w/w to about 45% w/w, or from about 2% w/w to about 40% w/w, or from about 2% w/w to about 35% w/w, or from about 2% w/w to about 30% w/w, or from about 2% w/w to about 25% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the methods and/or kits disclosed herein, wherein the hydrogen peroxide is at a concentration of about 0.1% w/w, or about 0.5% w/w, or about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods and/or kits disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the methods disclosed herein, wherein the first composition and/or the second composition may be used in combination with a gel or cream, which gel or cream may or may not further comprise hydrogen peroxide. In another aspect is provided any of the methods disclosed herein, wherein the first composition and/or the second composition may be used in combination with a gel or cream, which gel or cream does not further comprise hydrogen peroxide. In another aspect is provided any of the methods disclosed herein, wherein the first composition and/or the second composition may be used in combination with a gel or cream, which gel or cream further comprises hydrogen peroxide. Such gels or creams are generally commercially available and may contain from about 0.5% w/w to about 50% w/w hydrogen peroxide. For example, a gel containing about 1% w/w, or about 2% w/w, or about 3% w/w, or about 4% w/w, or about 6% w/w, or about 7% w/w, or about 8% w/w, or about 9% w/w, or about 10% w/w, or about 15% w/w, or about 20% w/w, or about 25% w/w, or about 30% w/w, or about 40% w/w, or about 45% w/w, or about 50% w/w hydrogen peroxide may be used in any of the methods disclosed herein in combination with the first composition and the second composition.

In another aspect is provided any of the methods or kits disclosed herein, wherein the *Spongilla* is *Spongilla lacustris*.

In another aspect is provided any of the methods disclosed herein, wherein the second composition comprising one or more fluidizing agents is applied topically to the skin of the subject. In another aspect is provided any of the methods disclosed herein, wherein the second composition is applied to the skin of the subject in the form of a solution. In another aspect is provided any of the methods disclosed herein, wherein the second composition comprising one or more fluidizing agents is applied to the skin of the subject in the form of an aqueous solution. Solutions of fluidizing agents, including aqueous solutions, may be prepared by methods known to those of ordinary skill in the art. For example, a hydrogen peroxide solution may be commercially available or prepared by methods known to those having ordinary skill in the art.

The mixture of *Spongilla* and the one or more fluidizing agents may be topically applied to the skin of a subject by drawing an appropriate amount of the mixture of *Spongilla* and the one or more fluidizing agents from a container and then applying the mixture to the skin of the subject by an appropriate method, such as by means of a sponge, a swab, a foam tipped stick, a cotton ball, a brush, a woven or non-woven fabric, roller, gauze, a pen, a glove, a finger, or the like.

In another aspect is provided any of the methods disclosed herein, wherein the amount of the first composition comprising *Spongilla* applied to the skin of the subject is from about 0.5 grams to about 50 grams. In one aspect is provided any of the methods disclosed herein, wherein the amount of the first composition is measured as a dry weight. In another aspect is provided any of the methods disclosed herein, wherein the amount of the first composition comprising *Spongilla* applied to the skin of the subject is from about 0.5 grams to about 40 grams, or from about 0.5 grams to about 35 grams, or from about 0.5 grams to about 30 grams, or from about 0.5 grams to about 25 grams, or from about 0.5 grams to about 20 grams, or from about 0.5 grams to about 15 grams, or from about 0.5 grams to about 10 grams, or from about 0.75 grams to about 20 grams, or from about 0.75 grams to about 15 grams, or from about 0.75 grams to about 10 grams, or from about 1 gram to about 20 grams, or from about 1 gram to about 15 grams, or from about 1 gram to about 10 grams, or from about 1 gram to about 9 grams, or from about 1 gram to about 8 grams, or from about 1 gram to about 7 grams, or from about 1 gram to about 6 grams, or from about 1 gram to about 5 grams, or from about 1 gram to about 4 grams, or from about 1 gram to about 3 grams, or from about 1 gram to 2 grams. In another aspect is provided any of the methods disclosed herein wherein the amount of *Spongilla* applied to the skin, such as those disclosed above, are each measured as a dry weight.

In another aspect is provided any of the methods disclosed herein, wherein the amount of the first composition comprising *Spongilla* applied to the skin of the subject is about 0.5 grams, or about 0.75 grams, or about 1 gram, or about 1.25 grams, or about 1.5 grams, or about 1.75 grams, or about 2 grams, or about 2.25 grams, or about 2.5 grams, or about 2.75 grams, or about 3 grams, or about 3.25 grams, or about 3.5 grams, or about 3.75 grams, or about 4 grams, or about 4.25 grams, or about 4.5 grams, or about 4.75 grams, or about 5 grams, or about 5.25 grams, or about 5.5 grams, or about 5.75 grams, or about 6 grams, or about 6.25 grams, or about 6.5 grams, or about 7 grams, or about 7.25 grams, or about 7.5 grams, or about 7.75 grams, or about 8 grams, or about 8.25 grams, or about 8.5 grams, or about 8.75 grams, or about 9 grams, or about 9.25 grams, or about 9.5 grams, or about 9.75 grams, or about 10 grams, or about 11 grams, or about 12 grams, or about 13 grams, or about 14 grams, or about 15 grams, or about 16 grams, or about 17 grams, or about 18 grams, or about 19 grams, or about 20 grams, or about 25 grams, or about 35 grams, or about 40 grams, or about 45 grams, or about 50 grams, or about 75 grams, or about 100 grams, or about 250 grams, or about 500 grams, or about 750 grams, or about 1000 grams, in each case measured as a dry weight. In another aspect is provided any of the methods disclosed herein, wherein the amount of the first composition comprising *Spongilla* applied to the skin of the subject is about 2 grams.

In another aspect is provided any of the methods disclosed herein, wherein the first composition is applied to the skin of the subject prior to the second composition being applied to the skin of the subject. In another aspect is provided any of the methods disclosed herein, wherein the first composition is applied to the skin of the subject and is permitted to dry on the skin of the subject prior to application of the second composition to the skin of the subject. In another aspect is provided any of the methods disclosed herein, wherein the first composition is applied to the skin of the subject in the form of an aqueous paste, wherein the aqueous component may be water or saline. In another aspect is provided any of the methods disclosed herein, wherein the aqueous paste further comprises hydrogen peroxide. In another aspect is provided any of the methods disclosed herein, wherein an aqueous solution of hydrogen peroxide is applied to the face of the subject following application of the first composition to the skin of the subject and prior to the application of the second composition to the skin of the subject. In another aspect is provided any of the methods disclosed herein, wherein the first composition further comprises hydrogen peroxide. In another aspect is provided any of the methods disclosed herein, wherein the hydrogen peroxide is an aqueous solution. In another aspect is provided any of the methods disclosed herein, wherein the aqueous solution comprises hydrogen peroxide at a w/w concentration of about 3%. In another aspect is provided any of the methods disclosed herein, wherein the second composition is permitted to dry on the skin of the subject following application to the skin of the subject. In another aspect is provided any of the methods disclosed herein, wherein the one or more fluidizing agents is water, saline, or a hydrogen peroxide solution.

In another aspect is provided any of the methods disclosed herein, wherein the first composition and the second composition are mixed together and the resulting mixture is applied to the skin of the subject. In another aspect is provided any of the methods disclosed herein, wherein the first composition comprising *Spongilla* and the second composition comprising an aqueous solution of hydrogen peroxide are mixed together and the resulting mixture is applied to the skin of the subject in need of treatment. In other aspects are provide the methods wherein the second composition comprises an aqueous solution of hydrogen peroxide having a concentration of hydrogen peroxide as disclosed herein, such as about 3% w/w. In another aspect are provided the methods wherein the *Spongilla* and the aqueous hydrogen peroxide, such as a 3% w/w solution of hydrogen peroxide, are mixed together and are applied to the skin of the subject in need of treatment. In some aspects, the mixture resulting from mixing the first composition comprising *Spongilla* and the second composition comprising an aqueous solution of hydrogen peroxide, such as a 3% solution of hydrogen peroxide, is allowed to stand for at least 10 seconds, at least 20 seconds, at least 30 seconds, at least 40 seconds, at least 45 seconds, at least 50 seconds, at least one minute, at least 90 seconds, at least 2 minutes, at least 2.5 minutes, at least 3 minutes, at least 3.5 minutes, at least 4 minutes, at least 4.5 minutes, at least 5 minutes, at least 5.5 minutes, at least 6 minutes, at least 6.5 minutes, at least 7 minutes, at least 7.5 minutes, at least 8 minutes, at least 8.5 minutes, at least 9 minutes, at least 10 minutes, at least 15 minutes, at least 30 minutes, at least 45 minutes, or about 1 hour prior to applying it the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 1 minute prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 1.5 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 2 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 2.5 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 3 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 4 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 5 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 6 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 7 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 8 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 9 minutes prior to application to the skin of the subject in need of treatment. In one aspect, the mixture resulting from mixing the first composition comprising *Spongilla* and the second composition comprising an aqueous solution of hydrogen peroxide, such as a 3% solution of hydrogen peroxide, is allowed to stand for 10 minutes prior to application to the skin of the subject in need of treatment.

In another aspect is provided any of the methods disclosed herein, wherein the composition comprising *Spongilla* and the one or more fluidizing agents is applied to the skin of the subject at least once per week for at least one week. In another aspect is provided any of the methods disclosed herein, wherein the composition comprising *Spongilla* and one or more fluidizing agents is applied to the skin of the subject at least at least two times per week for at least one week, at least three times per week for at least one week, at least 4 times per week for at least one week, at least 5 times per week for at least one week, at least 6 times per week for at least one week, or at least 7 times per week for at least one week. In another aspect is provided any of the methods disclosed herein, wherein the one or more fluidizing agents is water, saline, or a hydrogen peroxide solution. In another aspect is provided any of the methods disclosed herein, wherein the one or more fluidizing agents is 3% w/w hydrogen peroxide solution.

In another aspect is provided any of the methods disclosed herein, wherein the composition comprising *Spongilla* and one or more fluidizing agents is applied to the skin of the subject at least once per week for at least two weeks. In another aspect is provided any of the methods disclosed herein, wherein the composition comprising *Spongilla* and one or more fluidizing agents is applied to the skin of the subject at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the composition comprising Spongilla and one or more fluidizing agents is applied to the skin of the subject once per week for 6 weeks. In another aspect is provided any of the methods disclosed herein, wherein the one or more fluidizing agents is water, saline, or a hydrogen peroxide solution. In another aspect is provided any of the methods disclosed herein, wherein the one or more fluidizing agents is 3% w/w hydrogen peroxide solution.

In another aspect is provided any of the methods disclosed herein, wherein the composition comprising the mixture of Spongilla and the one or more fluidizing agents is applied to the skin of the subject at least once per week for at least two weeks. In another aspect is provided any of the methods disclosed herein, wherein the composition comprising the mixture of Spongilla and the one or more fluidizing agents is applied to the skin of the subject at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the composition comprising the mixture of Spongilla and the one or more fluidizing agents is applied to the skin of the subject once per week for 6 weeks. In another aspect is provided any of the methods disclosed herein, wherein the one or more fluidizing agents is water, saline, or a hydrogen peroxide solution. In another aspect is provided any of the methods disclosed herein, wherein the one or more fluidizing agents is 3% w/w hydrogen peroxide solution.

In another aspect is provided any of the methods disclosed herein, wherein the composition comprising the mixture of Spongilla and the one or more fluidizing agents is applied to the skin of the subject on at least one of the subject's face, back and chest. In another aspect is provided any of the methods disclosed herein, wherein the composition comprising the mixture of Spongilla and the one or more fluidizing agents is applied to the skin of the subject on the subject's face. In another aspect is provided any of the methods disclosed herein, wherein the composition comprising the mixture of Spongilla and the one or more fluidizing agents is applied to the skin of the subject on the subject's back. In another aspect is provided any of the methods disclosed herein, wherein the composition comprising the mixture of Spongilla and the one or more fluidizing agents is applied to the skin of the subject on the subject's chest. In another aspect is provided any of the methods disclosed herein, wherein the one or more fluidizing agents is water, saline, or a hydrogen peroxide solution. In another aspect is provided any of the methods disclosed herein, wherein the one or more fluidizing agents is 3% w/w hydrogen peroxide solution.

In another aspect is provided any of the methods disclosed herein, wherein the skin of the subject is cleaned using a non-comedogenic cleanser, water, or a combination of a non-comedogenic cleanser and water following application of the composition comprising Spongilla and one or more fluidizing agents. In another aspect is provided any of the methods disclosed herein, wherein the skin of the subject is cleaned using a non-comedogenic cleanser, water, or a combination of a non-comedogenic cleanser and water following application of the second composition to the skin of the subject. Non-comedogenic cleansers are those formulated not to cause blocked pores in the skin of subjects to which such cleansers are applied.

In another aspect is provided any of the methods disclosed herein, wherein the skin condition in the subject is selected from acne vulgaris, moderate acne vulgaris, or severe acne vulgaris. In another aspect is provided any of the methods disclosed herein, wherein the skin condition is acne vulgaris. In another aspect is provided any of the methods disclosed herein, wherein the skin condition in the subject is moderate acne vulgaris. In another aspect is provided any of the methods disclosed herein, wherein the skin condition in the subject is severe acne vulgaris.

In another aspect is provided any of the methods disclosed herein, wherein the skin condition in the subject is selected from facial acne vulgaris, moderate facial acne vulgaris, or severe facial acne vulgaris. In another aspect is provided any of the methods disclosed herein, wherein the skin condition is facial acne vulgaris. In another aspect is provided any of the methods disclosed herein, wherein the skin condition in the subject is moderate facial acne vulgaris. In another aspect is provided any of the methods disclosed herein, wherein the skin condition in the subject is severe facial acne vulgaris.

In another aspect is provided a method of treating a skin condition in a subject, comprising applying to the skin of the subject a first composition comprising Spongilla, and a second composition comprising one or more fluidizing agents, wherein (a) the one or more fluidizing agents comprises water, saline, or a hydrogen peroxide solution; and (b) the skin condition in the subject is selected from acne vulgaris, moderate facial acne vulgaris, or severe facial acne vulgaris. In another aspect is provided any of the methods disclosed herein, wherein the skin condition is facial acne vulgaris. In another aspect is provided any of the methods disclosed herein, wherein the skin condition in the subject is moderate facial acne vulgaris. In another aspect is provided any of the methods disclosed herein, wherein the skin condition in the subject is severe facial acne vulgaris. In another embodiment are methods, wherein the Spongilla is Spongilla lacustris. In another embodiment are methods, wherein the second composition is applied to the skin of the subject in the form of a solution. In another embodiment are methods, wherein the second composition is in the form of an aqueous solution. In another embodiment are methods wherein the hydrogen peroxide solution is a 3% hydrogen peroxide solution. In another embodiment are methods, wherein the amount of the first composition comprising *Spongilla* applied to the skin of the subject is from about 0.5 grams to about 50 grams, measured as a dry weight. In another embodiment are methods, wherein the first composition is applied to the skin of the subject in the form of a paste. In another embodiment are methods, wherein the paste further comprises water or saline. In another embodiment are methods, wherein the paste is prepared by mixing a powder comprising *Spongilla* and an aqueous solution comprising hydrogen peroxide. In another embodiment are methods, wherein the aqueous solution comprises hydrogen peroxide at a w/w concentration of about 3%. In another embodiment are methods, wherein the first composition is applied to the skin of the subject prior to the second composition being applied to the skin of the subject. In another embodiment are methods, wherein the first composition is applied to the skin of the subject and is permitted to dry on the skin of the subject prior to application of the second composition to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject and prior to the application of the second composition to the skin of the subject. In another embodiment are methods, wherein the first composition further comprises hydrogen peroxide. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the second composition is permitted to dry on the skin of the subject following application to the skin of the subject. In another embodiment are methods, wherein the second composition is applied to the skin of the subject prior to the first composition being applied to the skin of the subject. In another embodiment are methods, wherein the second composition is permitted to dry on the skin of the subject prior to the first composition being applied to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the first composition is permitted to dry on the skin of the subject. In another embodiment are methods, wherein the first composition and the second composition are mixed together, and the resulting mixture is applied to the skin of the subject. In another embodiment are methods, wherein the first composition is mixed with an aqueous solution of hydrogen peroxide prior to mixing with the second composition. In another embodiment are methods, wherein the mixture of the first composition and the second composition is further mixed with an aqueous solution of hydrogen peroxide prior to application to the skin of the subject. In another embodiment are methods, wherein the aqueous solution comprises hydrogen peroxide at a w/w concentration of about 3%. In another embodiment are methods, wherein the first composition and the second composition are applied to the skin of the subject once per week. In another embodiment are methods, wherein the second composition is applied to the skin of the subject no more than once every 4 weeks. In another embodiment are methods, wherein the first composition is applied to the skin of the subject at least once per week for at least one week. In another embodiment are methods, wherein the first composition is applied to the skin of the subject once per week for 6 weeks. In another embodiment are methods, wherein the first composition and the second composition are applied to the skin of the subject on at least one of the subject's face, back and chest. In another embodiment are methods, wherein the first composition and the second composition are applied to the skin of the subject on the subject's face. In another embodiment are methods, wherein the first composition and the second composition are applied to the skin of the subject on the subject's back. In another embodiment are methods, wherein the first composition c and the second composition comprising are applied to the skin of the subject on the subject's chest.

In another aspect is provided a kit, comprising a first composition and a second composition, wherein (a) the first composition comprises a *Spongilla*; and (b) the second composition comprises one or more fluidizing agents as described herein. In another aspect the one or more fluidizing agents is 3% w/w hydrogen peroxide solution. In another aspect is provided any of the kits described herein, further comprising instructions for use in treating a subject having a skin condition using the first and the second composition in the treatment. In another aspect is provided any of the kits described herein, wherein the first composition comprises *Spongilla* in the form of a powder. In another aspect is provided any of the kits described herein, wherein the *Spongilla* is in the form of a powder comprising particles that are substantially uniform in size.

In another aspect is provided any of the methods or kits described herein, wherein not less than 50% of the particles comprising the *Spongilla* powder pass through a US 70-mesh screen.

In another aspect is provided any of the methods or kits disclosed herein, wherein the first composition further comprises an aqueous solution of hydrogen peroxide. In another aspect is provided any of the methods or kits disclosed herein, wherein the hydrogen peroxide is at a concentration of from about 0.1% w/w to about 50% w/w, or from about 0.1% w/w to about 45% w/w, or from about 0.1% w/w to about 40% w/w, or from about 0.1% w/w to about 35% w/w, or from about 0.10% w/w to about 30% w/w, or from about 0.10% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 45% w/w, or from about 1% w/w to about 45% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 8% w/w, or from about 1% w/w to about 7% w/w, or from about 1% w/w to about 6% w/w, or from about 1% w/w to about 5% w/w, or from about 1% w/w to about 4% w/w, or from about 1% w/w to about 3% w/w, or from about 1% w/w to about 2% w/w, or from about 2% w/w to about 45% w/w, or from about 2% w/w to about 40% w/w, or from about 2% w/w to about 35% w/w, or from about 2% w/w to about 300% w/w, or from about 2% w/w to about 250% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the methods or kits disclosed herein, wherein the hydrogen peroxide is at a concentration of about 0.1% w/w, or about 0.5% w/w, or about 1% w/w, or about 2% w/w, or about 30% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the methods or kits disclosed herein, further comprising a gel or cream comprising hydrogen peroxide. Such gels or creams are generally commercially available any may contain from about 0.5% w/w to about 50% w/w hydrogen peroxide. For example, a gel containing about 1% w/w, or about 2% w/w, or about 3% w/w, or about 4% w/w, or about 6% w/w, or about 7% w/w, or about 8% w/w, or about 9% w/w, or about 10% w/w, or about 15% w/w, or about 20% w/w, or about 25% w/w, or about 30% w/w, or about 40% w/w, or about 45% w/w, or about 50% w/w hydrogen peroxide may be used in any of the methods and methods or kits disclosed herein in combination with the first composition and the second composition.

In another aspect is provided any of the methods or kits disclosed herein, wherein the *Spongilla* is *Spongilla lacustris*.

In another aspect is provided any of the kits described herein, wherein the kit is used for the treatment of a skin condition in a subject. In another aspect is provided any of the kits described herein, wherein the kit is for use in the treatment of a skin condition in a subject. In another aspect is provided any of the kits described herein, wherein the skin condition in the subject is selected from acne vulgaris, moderate facial acne vulgaris, or severe facial acne vulgaris. In another aspect is provided any of the kits disclosed herein, wherein the skin condition is facial acne vulgaris. In another aspect is provided any of the kits disclosed herein, wherein the skin condition in the subject is moderate facial acne vulgaris. In another aspect is provided any of the kits disclosed herein, wherein the skin condition in the subject is severe facial acne vulgaris.

In another embodiment are provided methods to treat, reduce the symptoms of, ameliorate the symptoms of, delay the onset of, or otherwise pharmaceutically address acne vulgaris, moderate acne vulgaris, severe acne vulgaris, facial acne vulgaris, moderate facial acne vulgaris, severe facial acne vulgaris. In another aspect is provided any of the kits disclosed herein, wherein the skin condition is acne vulgaris. In another aspect is provided any of the kits disclosed herein, wherein the skin condition is moderate acne vulgaris. In another aspect is provided any of the kits disclosed herein, wherein the skin condition is severe acne vulgaris. In another aspect is provided any of the kits disclosed herein, wherein the skin condition is facial acne vulgaris. In another aspect is provided any of the kits disclosed herein, wherein the skin condition is moderate facial acne vulgaris. In another aspect is provided any of the kits disclosed herein, wherein the skin condition is severe facial acne vulgaris.

The compositions disclosed herein, such as the composition comprising *Spongilla* and one or more fluidizing agents, may further comprise one or more conventional pharmaceutical carriers or excipients. Suitable pharmaceutical carriers and excipients include inert diluents, binders (such as starches), fillers (such as colloidal silicon dioxide, sugars, including lactose, sucrose, mannitol, or sorbitol; and cellulose preparations, for example, maize starch, wheat starch, rice starch, potato starch, gelatin, gum, methyl cellulose, hydroxypropyl methyl cellulose, sodium carboxymethylcellulose, or polyvinylpyrrolidone (PVP)), bulking agents, lubricants (such as magnesium stearate, sodium lauryl sulfate and talc), coloring matters or dyes and, if desired, emulsifying agents or suspending agents, together with diluents such as water, saline, ethanol, propylene glycol, glycerin, or combinations thereof.

The pharmaceutical compositions disclosed herein may be in unit dosage forms suitable for single administration of precise dosages. In another aspect is provided any of the methods or kits disclosed herein, wherein the unit dosage forms of the first compositions and/or the second composition are suitable for two administrations, three administrations, four administrations, five administrations, six administrations, seven administrations, eight administrations, 10 administrations, 11 administrations, 12 administrations, 13 administrations, 14 administrations, 15 administrations, 16 administrations, 17 administrations, 18 administrations, 19 administrations, 20 administrations, 21 administrations, 22 administrations, 23 administrations, 24 administrations, 25 administrations, 26 administrations, 27 administrations, 28 administrations, 29 administrations, 30 administrations, administrations for two months, administrations for three months, administrations for four months, administrations for five months, administrations for six months, administrations for seven months, administrations for eight months, administrations for nine months, administrations for ten months, administrations for eleven months, or administrations for 12 months.

It will be appreciated that the actual dosages of the compositions disclosed herein, may vary according to the composition being used, the mode of administration, and the particular site of the subject being treated, and the skin condition being treated. Those skilled in the art using conventional dosage-determination tests in view of the experimental data for a given composition may ascertain optimal dosages for a given set of conditions. This amount will vary depending upon a variety of factors, including but not limited to the characteristics of the compositions and formulations disclosed herein (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier mg/kg or carriers in the formulation, and the route of administration. Further, an effective or therapeutically effective amount may vary depending on whether the one or more compositions and formulations disclosed herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more compositions and formulations disclosed herein and adjusting the dosage accordingly.

Dosage regimens using the first composition and the second composition may be adjusted to provide the optimum desired response. Dosage unit form, as used herein, refers to physically discrete units suited as unitary dosages for the subjects to be treated; each unit containing a predetermined quantity of the compositions disclosed herein, calculated to produce the desired therapeutic effect in association with the required pharmaceutical carrier. The specification for the dosage unit forms of the compositions disclosed herein are dictated by and directly dependent on (a) the characteristics of the composition and the particular therapeutic or prophylactic effect to be achieved, and (b) the limitations inherent in the art of compounding such a composition for the treatment a particular condition in a subject.

Thus, the skilled artisan would appreciate, based upon the disclosure provided herein, that the dose and dosing regimen using the compositions disclosed herein may be adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the presently disclosed methods.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. The embodiments disclosed herein are intended to encompass intra-subject dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

In some embodiments, the compositions may be used in combination with one or more additional compositions useful in treating skin conditions in a subject which are described below. When a combination therapy is used, the one or more additional compositions may be administered sequentially or simultaneously with the first composition and/or the second composition disclosed herein. In some embodiments, the additional compositions is administered to a subject prior to, at the same time as, or following administration of the first composition and/or the second composition disclosed herein. In some embodiments, the additional composition is administered to the subject prior to the administration of the first composition and/or the second composition disclosed herein. In some embodiments, the additional composition is administered to the subject at the same time the first composition and/or the second composition disclosed herein are administered to the subject. In some embodiments, the additional composition is administered to the subject following the administration of the first composition and/or the second composition disclosed herein. Among the additional compositions that may be used according to any of the methods disclosed herein include, but are not limited to, cromolyn sodium (also known as sodium cromoglycate), topical alpha agonists (including, but not limited to, oxymetazoline hydrochloride, clonidine hydrochloride, apraclonidine hydrochloride, and brimonidine tartrate), topical antibiotics (including, but not limited to, tetracyclines [tetracycline, doxycycline, minocycline, sarecycline], clindamycin, and erythromycin), benzoyl peroxide, salicylic acid, azelaic acid, retinoids, topical anticholinergics (including, but not limited to, oxybutynin, glycopyrrolate, propantheline), topical prostaglandin analogs (including, but not limited to, latanoprost, bimatoprost, travoprost, and tafluprost), and topical hydroquinone or a combination of fluocinolone acetonide, hydroquinone, and tretinoin (sold as Tri-Luma® cream).

In another aspect is provided any of the methods disclosed herein, wherein the *Spongilla* is *Spongilla lacustris*. In another aspect is provided any of the kits disclosed herein, wherein the *Spongilla* is *Spongilla lacustris*.

As will be understood by one skilled in the art, for all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented.

The preparations and examples of a number of embodiments disclosed herein are intended to be illustrative and not limiting. All starting materials are available commercially or are described in the literature. All temperatures are reported in ° C.

Example 1: Preparation of *Spongilla* Materials

*Spongilla* raw material was treated with heat or gamma irradiation to reduce bioburden to acceptable levels. The resulting materials were milled and sieved to obtain a material having a particle size of no larger than 200 µm. The sized material was dried using a low temperature tray dryer at a temperature of about 40° C. to obtain a target moisture content of less than 1%. A representative batch of materials was irradiated as follows using Nordion Cobalt-60 Batch JS 8900 Irradiator #139, ON-STD; processing start time=10: 57:38 am; processing end time: 01:31:14 pm; minimum specified dose (kGy): 25.0; maximum specified dose (kGy): 32.5; minimum delivered dose (kGy): 26.2; maximum delivered dose (kGy): 31.2. The resulting material was filled and sealed into high-density polyethylene jars that were packaged into foil laminate pouches containing desiccant packets. The packaged product may be further gamma irradiated if the material does not otherwise meet the microbial limits set forth in USP <1111>. The resulting materials were stored at a temperature of below 30° C. and were protected from light and moisture prior to use.

The subjects were randomly assigned to one of four treatment groups as outlined in Table 1. Subjects in Group 1 were administered a composition comprising *Spongilla* powder (2 grams) mixed with 3% hydrogen peroxide USP (6 mL) for each application. Subjects in Group 2 were administered placebo (kelp powder) mixed with 3% hydrogen peroxide USP (6 mL) for each application. Subjects in Group 3 were administered *Spongilla* mixed with purified water for each application. Subjects in Group 4 were administered placebo (kelp powder) mixed with purified water for each application. The study medication was administered to the entire face of the subject up to once-weekly for 12 weeks in both the clinic by trained study staff, and at home by the subject after thorough training. Treatments were applied in the clinic once-weekly for the first 5 weeks of treatment (Days 1 through 29) and then subjects were allowed to apply treatments at home for the next 1 to 3 weeks (Days 36, 43, and 50) based on their Day 29 IGA score. Subjects returned to the clinic on Day 57 and treatment was applied in the clinic. Subsequently, subjects were permitted to apply a treatment at home for the next week (Day 64) depending on their Day 57 IGA score. Subjects returned to the clinic for their final treatments on Day 71 and 78, providing they met the treatment criteria. No serious adverse events were reported in treatment groups 1, 3, or 4. Two subjects in treatment group 2 reported serious adverse events, one reported cholecystitis and the other reported a ruptured ovarian cyst, neither of which was considered related to treatment.

TABLE 1

Treatment Allocation

| Group | Study Treatment | No. of Subjects | No. Subjects Reporting at least one Adverse Event | No. Subjects Reporting at least one Serious Adverse Event | No. Subjects Not Completing Study |
|---|---|---|---|---|---|
| 1 | *Spongilla* powder mixed with 3% peroxide USP | 29 | 8 (27.6%) | 0 | 7 (24.1%) |
| 2 | Placebo control powder (kelp powder) mixed with 3% peroxide USP | 30 | 6 (20%) | 2 (6.7%) | 5 (16.7%) |
| 3 | *Spongilla* powder mixed with purified water | 32 | 5 (15.6%) | 0 | 8 (25%) |
| 4 | Placebo control powder (kelp powder) mixed with purified water | 30 | 5 (16.7%) | 0 | 9 (30%) |

Example 2: Study of Tolerability, Safety and Efficacy of *Spongilla* in Patients with Acne Vulgaris The study was conducted in compliance with International Conference on Harmonisation (ICH) Good Clinical Practices (GCPs). The objective of the study was to evaluate the tolerability, safety, and efficacy of *Spongilla* topical powder obtained according to Example 1, or a process similar to that set forth in Example 1, mixed with 3% hydrogen peroxide USP, following 12 weeks of topical administration (up to once-weekly treatments) in male and female patients with moderate to severe facial acne vulgaris. The study employed a 2×2 factorial design in order to assess the contribution of each component of the treatment, *Spongilla* topical powder and 3% hydrogen peroxide USP.

The study was structured as a randomized, double-blind, 2×2 factorial, placebo-controlled study of approximately 12 weeks (day 1 randomization/treatment to day 85 study exit).

Randomization/Stratification: On day 1 at each investigational site, patients were randomly assigned to 1 of 4 treatment groups in a 1:1:1:1 ratio to receive one of the four treatments in Table 1.

Visit Schedule: Each patient was permitted in the study for up to approximately 16 weeks. Patients had 28 days to meet study criteria (i.e., Screening) before entering the 84-day treatment period. Visit 1 (Day −28 to −1): Screening; Visit 2 (Day 1): Baseline, randomization, and treatment initiation; Visits 3-5 (Days 8, 15, and 22): Weekly follow-up visits; Visits 6-7 (Days 29 and 57): Monthly follow-up visits; Visits 8-9 (Days 71 and 78): Weekly Treatment Visits; Visit 10 (day 85 [successful completion of study] or early discontinuation): Exit Study Population: Approximately 121 patients were enrolled who were male and female patients, 12 years or older, with moderate to severe acne vulgaris with facial involvement who are in otherwise good health. Female patients had to be non-pregnant at the time of consent.

Patients had moderate to severe acne vulgaris defined as meeting all of the following criteria (a) a minimum of 20 but not more than 50 inflammatory lesions (papules and pustules) on the face; (b) a minimum of 20 but not more than 100 noninflammatory lesions (open comedones and closed comedones) on the face; and (c) an investigator's Global Assessment (IGA) score of 3 or 4 as assessed by the investigator (the area considered for the IGA must be confined to the face). Among the exclusion criteria were: (a) the subject was pregnant, lactating, or was planning to become pregnant during the study; (b) the subject was diagnosed with acne excoriate, acne conglobate, acne fulminans, secondary acne (e.g., chloracne, iatrogenic acne, and drug-induced acne), or 1 or more nodule or cyst above the mandibular line; (c) in the opinion of the investigator, the patient had a skin pathology or condition (such as basal cell carcinoma) that could interfere with the evaluation of the test products or required the use of interfering topical or systemic therapy during the study; (d) the subject had a history of severe allergic reactions or anaphylaxis to any allergen or the patient has a history of allergic reactions to shellfish or iodine, regardless of the severity, where the allergic reaction was considered severe if it is prolonged (e.g., not rapidly responsive to symptomatic medication), there is a recurrence of symptoms following initial improvement, or hospitalization was indicated for clinical sequelae (e.g., renal impairment, pulmonary infiltrates).

Treatment regimens: The treatment products for each cohort of subjects in the study is shown in Table 2. The *Spongilla lacustris* powder was used after addition of 6 mL of 3% hydrogen peroxide USP or 6 mL of purified water. To ensure the blinding of the study, the placebo (kelp powder) was chosen due to similar texture, color and smell to the *Spongilla lacustris*. Additionally, the *Spongilla* powder and the placebo kelp powder were supplied in identical packaging. The 3% hydrogen peroxide USP and purified water were packaged with blinding labels covering the entire pouch.

TABLE 2

Treatment Products for each subject cohort

| Product name | Spongilla powder plus hydrogen peroxide<br>2 gm of *Spongilla* powder<br>6 mL of 3% hydrogen peroxide USP |
|---|---|
| Product name | Spongilla powder plus water<br>2 gm of *Spongilla* powder<br>6 mL of purified water |
| Product name | Kelp powder plus hydrogen peroxide<br>2 gm of kelp powder (FCC)<br>6 mL of 3% $H_2O_2$ USP |
| Product name | Kelp powder plus water<br>2 gm kelp powder<br>6 mL of purified water |

The products were applied to the entire face of each subject up to once weekly for up to 84 days. The products were applied in the clinic at Visits 2-6 by the study staff. Subjects were permitted to apply the products to their entire face at home on days 36, 43, 50, and 64. Subjects washed his/her face with mild facial cleanser (e.g., Cetaphil®) and water and then gently dried the area. The powder and the fluidizing agent applicable to each treatment regimen disclosed in Table 2 were mixed together using a metal or wooden instrument, such as a spatula, and the resulting mixture was permitted to stand for approximately 1 minute to 5 minutes before it was applied to the subject's face by spreading it onto the subject's face and gently massaging into the skin. The mixture was then washed from the patient's face after about 15 minutes following application.

Efficacy was measured by determining lesion counts (inflammatory and noninflammatory) on the face by the investigator or an appropriately trained designee. The total number of lesions in the area to be treated, absolute changes from baseline in total, inflammatory, and non-inflammatory lesion counts were determined for each subject. The total Investigator's Global Assessment (IGA) acne severity scale score for each subject was determined by reference to Table 3, below, prior to treatment and following completion of the treatment regimen. Treatment success was defined as the proportion of patients achieving a grade of zero or 1 on the IGA.

Table 3: Investigator's Global Assessment (IGA) acne severity scale

| Score | Grade | Description |
|---|---|---|
| 0 | None | No evidence of facial acne vulgaris |
| 1 | Minimal | Few noninflammatory lesions (comedones) are present; a few inflammatory lesions(papules/pustules) may be present; no nodulo-cystic lesions are allowed) |
| 2 | Mild | Several to many noninflammatory lesions (comedones) are present; a few inflammatory lesions (papules/pustules) are present; no nodulo-cystic lesions are allowed |
| 3 | Moderate | Many noninflammatory (comedones) and inflammatory lesions (papules/pustules) are present; no nodulo-cystic lesions are allowed |
| 4 | Severe | Significant degree of inflammatory disease; papules/pustules are a predominant feature; a few nodulo-cystic lesions may be present; comedones may be present |

The Dermatology Life Quality Index (DLQI) score was determined for each subject prior to treatment and after completion of the treatment regimen. The absolute change in total DLQI score was determined for each patient using the DLQI score for the subject prior to treatment as the baseline score.

All efficacy analyses were performed using the ITT and PP population. For lesion counts, absolute and percent change from baseline in lesion counts were summarized using descriptive statistics by treatment group. Between-group comparisons of change from baseline in lesion counts were performed based on an analysis of covariance (ANCOVA) model with the two factorial effects as factors, and lesion count at baseline as a covariate. The ANCOVA will allow for the assessment of the main effect of *Spongilla* powder and the main effect of 3% hydrogen peroxide, in addition to testing for the interaction of the two effects. A frequency distribution was used to analyze the proportion of patients with a score of clear (0) or almost clear (1) on the IGA by treatment group. The proportion of patients with a 2-grade improvement from baseline on the IGA by treatment group was analyzed in the same fashion. Between-group comparisons were performed using a chi-square analysis that account for both main effects and interactions of the interventions. Approximately 121 patients were randomized into the study in a 1:1:1:1 ratio yielding approximately 30 patients in each of the four intervention groups. The number of subjects was calculated to provide a sample size yielding 75% power to detect the difference between a proportion of 12% and 48% for a 2-grade improvement in the IGA. Additionally, this sample size had a 97% power to detect a difference in mean lesion counts of −11.0 (the difference between a group mean of −26.0 and a group mean of −15.0) assuming that the common standard deviation is 10.0 using a two-group t-test with a 0.050 two-sided significance level.

Results: The mean change from baseline in the count of the number of inflammatory lesions in the treatment groups treated with (a) *Spongilla* powder mixed with 3% peroxide USP, or (b) Placebo control powder (kelp powder) mixed with 3% peroxide USP are shown in Table 4. As shown, subjects experienced a statistically significant reduction baseline in the count of the number of inflammatory lesions in the treatment groups treated with *Spongilla* powder mixed with 3% peroxide USP compared to subjects treated with placebo control powder (kelp powder) mixed with 3% peroxide USP at days 57 and 85.

TABLE 4

Mean change from baseline in the count of the number of inflammatory lesions in subjects in treatment groups

| Day/ Treatment Group | Subjects treated with *Spongilla* powder mixed with 3% peroxide USP (N = 27) | Subjects treated with placebo control powder (kelp powder) mixed with 3% peroxide USP (N = 29) |
|---|---|---|
| Day 15 | −9.78 | −7.34 |
| Day 29 | −11.65 | −10.42 |
| Day 57 | −14.33* | −9.92 |
| Day 85/ET* | −15.83* | −12.4 |

*= p < 0.05

The mean change from baseline in the count of the number of non-inflammatory lesions in the treatment groups treated with (a) *Spongilla* powder mixed with 3% peroxide USP, or (b) Placebo control powder (kelp powder) mixed with 3% peroxide USP are shown in Table 5.

TABLE 5

Mean change from baseline in the count of the number of non-inflammatory lesions in subjects in treatment groups

| Day/ Treatment Group | Subjects treated with *Spongilla* powder mixed with 3% peroxide USP (N = 27) | Subjects treated with placebo control powder (kelp powder) mixed with 3% peroxide USP (N = 29) |
|---|---|---|
| Day 15 | −9.34 | −10.09 |
| Day 29 | −11.53 | −13.53 |
| Day 57 | −14.93 | −19.22 |
| Day 85/ET* | −14.4 | −18.22 |

The number of subjects in each of the four treatment groups experiencing a two-grade change in the Investigator's Global Assessment (IGA) Score following treatment is shown in Table 6. As shown, subjects treated with the mixture comprising *Spongilla* powder mixed with 3% hydrogen peroxide experienced a greater rate of two-grade change in the Investigator's Global Assessment (IGA) score following treatment than subjects in the other treatment groups. The result was clinically meaningful.

TABLE 6

Investigator's Global Assessment (IGA) Score Two-Grade Change

| IGA Score of 0 or 1 | *Spongilla* powder mixed with 3% peroxide USP (N = 27) | Placebo control powder (kelp powder) mixed with 3% peroxide USP (N = 29) | *Spongilla* powder mixed with purified water (N = 30) | Placebo control powder (kelp powder) mixed with purified water (N = 29) |
|---|---|---|---|---|
| Day 15 | 1 (3.8%) | 1 (3.4%) | 2 (7.1%) | 1 (3.7%) |
| Day 29 | 5 (18.5%) | 3 (10.3%) | 4 (13.3%) | 3 (10.3%) |
| Day 57 | 10 (37%) | 5 (17.2%) | 4 (13.3%) | 6 (20.7%) |
| Day 85/ET | 10 (37%) | 8 (27.6%) | 6 (20%) | 10 (34.5%) |
| Day 85* | 13 (48.2%) | 9 (31%) | 7 (23%) | 10 (34.5%) |

*Includes subjects who had a 2-grade change during the study, then went on a drug holiday and no longer had a 2-grade change at day 85.

The number of subjects in each treatment group that experienced a two-grade change in Investigator's Global Assessment (IGA) Score and an IGA of zero or one following treatment are shown in Table 7. As shown, subjects treated with the mixture comprising *Spongilla* powder mixed with 3% hydrogen peroxide experienced a greater rate of two-grade change in the Investigator's Global Assessment (IGA) score and an IGA score of zero or one following treatment than subjects in the other treatment groups. The result was clinically meaningful.

TABLE 7

Investigator's Global Assessment (IGA) Score Two-Grade Change and an IGA of Zero or One

| IGA Score of 0 or 1 | *Spongilla* powder mixed with 3% peroxide USP (N = 27) | Placebo control powder (kelp powder) mixed with 3% peroxide USP (N = 29) | *Spongilla* powder mixed with purified water (N = 30) | Placebo control powder (kelp powder) mixed with purified water (N = 29) |
|---|---|---|---|---|
| Day 15 | 1 (3.8%) | 1 (3.4%) | 2 (7.1%) | 1 (3.7%) |
| Day 29 | 4 (14.8%) | 3 (10.3%) | 4 (13.3%) | 3 (10.3%) |
| Day 57 | 8 (29.6%) | 5 (17.2%) | 4 (13.3%) | 6 (20.7%) |

TABLE 7-continued

Investigator's Global Assessment (IGA) Score Two-Grade Change and an IGA of Zero or One

| IGA Score of 0 or 1 | *Spongilla* powder mixed with 3% peroxide USP (N = 27) | Placebo control powder (kelp powder) mixed with 3% peroxide USP (N = 29) | *Spongilla* powder mixed with purified water (N = 30) | Placebo control powder (kelp powder) mixed with purified water (N = 29) |
|---|---|---|---|---|
| Day 85/ET | 8 (29.6%) | 8 (27.6%) | 6 (20%) | 10 (34.5%) |
| Day 85* | 11 (40.7%) | 9 (31%) | 7 (23.3%) | 10 (34.5%) |

*Includes subjects who had an IGA of zero or one & a 2-grade change during the study, then went on a drug holiday and no longer had an IGA of zero or one & a 2-grade change at day 85

The invention claimed is:

1. A method of treating acne vulgaris in a subject in need thereof, comprising applying to the skin of the subject a therapeutically effective amount of a first composition comprising *Spongilla* particles having an average diameter of from about 5 µm to about 50 µm, and an effective amount of a second composition comprising one or more fluidizing agents; wherein applying the therapeutically effective amount of the first composition and the therapeutically effective amount of the second composition to the skin of the subject treats acne vulgaris in the subject, and wherein the subject experiences at least a one-grade improvement in the Investigator's Global Assessment (IGA) acne severity scale following treatment.

2. A method for treating acne vulgaris in a subject in need thereof, comprising administering to the subject a therapeutically effective amount of a pharmaceutical composition comprising a first composition and a second composition, wherein the first composition comprises *Spongilla* particles having an average diameter of from about 5 µm to about 50 µm, and the second composition comprises one or more fluidizing agents, wherein the pharmaceutical composition is applied to an area of the skin of the subject in need of treatment to treat acne vulgaris in the subject, and wherein the subject experiences at least a one-grade improvement in the Investigator's Global Assessment (IGA) acne severity scale following treatment.

3. A method of reducing the number of acne vulgaris lesions on the skin of a subject in need thereof, comprising applying to an area of the skin of the subject in need of treatment a therapeutically effective amount of a mixture comprising *Spongilla* particles having an average diameter of from about 5 µm to about 50 µm and one or more fluidizing agents; wherein applying the therapeutically effective amount of the mixture treats acne vulgaris in the subject, and wherein the subject experiences at least a one-grade improvement in the Investigator's Global Assessment (IGA) acne severity scale following treatment.

4. The method according to claim 1, wherein the subject experiences a reduction in the total number of acne vulgaris lesions following treatment.

5. The method according to claim 1, wherein the total number of acne vulgaris lesions on the skin of the subject is reduced by at least 10% following treatment.

6. The method according to claim 1, wherein the total number of acne vulgaris lesions on the skin of the subject is reduced by at least 20% following treatment.

7. The method according claim 1, wherein the subject experiences an improvement from baseline in the Investigator's Global Assessment (IGA) acne severity scale following treatment.

8. The method according to claim 1, wherein the subject has a score of 2 or less on the Investigator's Global Assessment (IGA) acne severity scale following treatment.

9. The method according to claim 1, wherein the one or more fluidizing agents is selected from water, saline, and a hydrogen peroxide solution.

10. The method according to claim 9, wherein the hydrogen peroxide solution is an aqueous solution.

11. The method according to claim 9, wherein the hydrogen peroxide solution is from about 0.5% by weight to about 50% by weight hydrogen peroxide.

12. The method according to claim 1, wherein treatment comprises one or more applications to the skin of the subject of the first composition comprising *Spongilla*, and the second composition comprising one or more fluidizing agents.

13. The method according to claim 1, wherein the first composition and the second composition are applied to the skin of the subject at least once per week.

14. The method according to claim 13, wherein the first composition and the second composition are applied to the skin of the subject at least once per week for one or more weeks.

15. The method according to claim 1, wherein the first composition and the second composition are applied to the skin of the subject once every two weeks.

16. The method according to claim 15, wherein the first composition and the second composition are applied to the skin of the subject once every two weeks for two or more weeks.

17. The method according claim 1, wherein the first composition comprises *Spongilla* in the form of a powder.

18. The method according to claim 17, wherein the *Spongilla* is in the form of a powder comprising particles that are substantially uniform in size.

19. The method according to claim 17, wherein not less than 50% of the particles comprising the *Spongilla* powder pass through a US 70-mesh screen.

20. The method according to claim 17, wherein the particles comprising the *Spongilla* powder have an average length of from about 50 µm to about 500 µm.

21. The method according to claim 18, wherein the particles comprising the *Spongilla* powder have an aspect ratio of from about 1 to 100.

22. The method according to claim 1, wherein the first composition has a residual moisture content of not more than about 10%.

23. The method according to claim 1, wherein the first composition has a combined aerobic and anaerobic microbial content of not more than about $25 \times 10^4$ colony-forming units per gram (CFU/g) and/or a combined yeast and mold content of not more than about $25 \times 10^4$ colony-forming units per gram (CFU/g).

24. The method according to claim 1, wherein the amount of Coliform bacteria, *Salmonella*, *Pseudomonas aeruginosa*, and/or *Staphylococcus aureus* bacteria in the first composition is not more than about $25 \times 10^4$ colony-forming units per gram (CFU/g).

25. The method according to claim 1, wherein the first composition was packaged prior to use.

26. The method according to claim 1, wherein the *Spongilla* is *Spongilla lacustris*.

27. The method according to claim 1, wherein the one or more fluidizing agents is applied to the skin of the subject in the form of a pharmaceutical composition comprising the one or more fluidizing agents and one or more pharmaceutically acceptable carriers or excipients.

28. The method according to claim 27, wherein the second composition is in the form of a solution, an aqueous solution, a powder, or a gel.

29. The method according to claim 1, wherein the amount of the first composition comprising *Spongilla* applied to the skin of the subject is from about 0.5 grams to about 50 grams.

30. The method according to claim 1, wherein the composition is applied to the skin of the subject in the form of a paste.

31. The method according to claim 30, wherein the paste further comprises water or saline.

32. The method according to claim 1, wherein the first composition and the second composition are mixed together and the resulting mixture is applied to the skin of the subject.

33. The method according to claim 1, wherein the acne vulgaris is moderate acne vulgaris or severe acne vulgaris.

34. The method according to claim 1, wherein the acne vulgaris is facial acne vulgaris.

35. The method according to claim 34, wherein the facial acne vulgaris is moderate facial acne vulgaris.

36. The method according to claim 34, wherein the facial acne vulgaris is severe facial acne vulgaris.

37. The method according to claim 1, wherein the subject is not diagnosed with acne excoriate, acne conglobata, acne fulminans, secondary acne, chloracne, iatrogenic acne, drug-induced acne, or 1 or more, or 2 or more, nodule or cyst above the mandibular line.

38. The method according to claim 1, wherein the subject has (a) a minimum of 20 but not more than 50 inflammatory lesions (papules and pustules) on the face; (b) a minimum of 20 but not more than 100 noninflammatory lesions (open comedones and closed comedones) on the face; and (c) an investigator's Global Assessment (IGA) score of 3 or 4 in the area of the skin to be treated.

39. The method according to claim 1, wherein the composition comprises about 2 gram of *Spongilla* and about 6 mL of 3% hydrogen peroxide.

40. The method according to claim 1, wherein the subject washes the composition from the skin within about 15 minutes following application.

41. The method according to claim 1, wherein the skin of the subject is cleaned using a non-comedogenic cleanser, water, or a combination of a non-comedogenic cleanser and water following application of the first composition comprising *Spongilla*.

42. The method of claim 1, wherein the composition comprises about 1 gram to about 25 grams of *Spongilla* and about 1 mL to about 50 mL of 3% hydrogen peroxide.

43. The method of claim 1, wherein the subject washes the composition from the skin within about 1 minute to about 180 minutes following application.

44. The method of claim 1, wherein the composition comprises about 2 grams of *Spongilla* and about 6 mL of 3% hydrogen peroxide, wherein the skin of the subject is cleaned with a non-comedogenic cleanser prior to application of the composition, and wherein the subject washes the composition from the skin within about 15 minutes following application.

* * * * *